United States Patent
Yang et al.

(10) Patent No.: US 11,078,462 B2
(45) Date of Patent: Aug. 3, 2021

(54) PERIVASCULAR STROMAL CELLS FROM PRIMATE PLURIPOTENT STEM CELLS

(71) Applicant: ReCyte Therapeutics, Inc., Alameda, CA (US)

(72) Inventors: Jiwei Yang, Palo Alto, CA (US); Dana Larocca, Alameda, CA (US); Midori Greenwood-Goodwin, Alameda, CA (US)

(73) Assignee: ReCyte Therapeutics, Inc., Alameda, CA (US)

(*) Notice: Subject to any disclaimer, the term of this patent is extended or adjusted under 35 U.S.C. 154(b) by 0 days.

(21) Appl. No.: 14/625,621

(22) Filed: Feb. 18, 2015

(65) Prior Publication Data

US 2015/0368609 A1  Dec. 24, 2015

Related U.S. Application Data

(60) Provisional application No. 62/014,639, filed on Jun. 19, 2014, provisional application No. 61/941,439, filed on Feb. 18, 2014.

(51) Int. Cl.
*C12N 5/077* (2010.01)
*C12N 5/0775* (2010.01)

(52) U.S. Cl.
CPC ......... *C12N 5/0662* (2013.01); *C12N 5/0652* (2013.01); *C12N 2501/115* (2013.01); *C12N 2501/15* (2013.01); *C12N 2501/155* (2013.01); *C12N 2501/165* (2013.01); *C12N 2502/28* (2013.01); *C12N 2506/02* (2013.01)

(58) Field of Classification Search
None
See application file for complete search history.

(56) References Cited

U.S. PATENT DOCUMENTS

| | | | |
|---|---|---|---|
| 5,030,015 A | 7/1991 | Baker et al. |
| 5,843,780 A | 12/1998 | Thomson |
| 5,922,601 A | 7/1999 | Baetscher et al. |
| 6,200,806 B1 | 3/2001 | Thomson |
| 6,248,934 B1 | 6/2001 | Tessier-Lavigne et al. |
| 6,280,718 B1 | 8/2001 | Kaufman et al. |
| 6,465,493 B1 | 10/2002 | Burgess et al. |
| 6,602,711 B1 | 8/2003 | Thomson et al. |
| 6,685,911 B1 | 2/2004 | Zitvogel et al. |
| 6,887,706 B2 | 5/2005 | Zhang et al. |
| 7,176,023 B2 | 2/2007 | Kaufman et al. |
| 7,217,569 B2 | 5/2007 | Thomson |
| 7,253,334 B2 | 8/2007 | Collas et al. |
| 7,417,041 B2 | 8/2008 | Blumberg et al. |
| 7,582,479 B2 | 9/2009 | Thomson |
| 7,625,573 B2 | 12/2009 | Zitvogel et al. |
| 7,736,895 B2 | 6/2010 | Collas et al. |
| 7,928,069 B2 | 4/2011 | Prestwich et al. |
| 7,951,591 B2 | 5/2011 | Robl et al. |
| 7,981,871 B2 | 7/2011 | Prestwich et al. |
| 8,021,847 B2 | 9/2011 | Pietrzkowski |
| 8,090,542 B2 | 1/2012 | Khvorova et al. |
| 8,247,384 B2 | 8/2012 | Green et al. |
| 8,324,184 B2 | 12/2012 | Prestwich et al. |
| 8,476,017 B2 | 7/2013 | Pietrzkowski |
| 8,685,386 B2 | 4/2014 | West et al. |
| 9,175,263 B2 | 11/2015 | Larocca et al. |
| 10,227,561 B2 | 3/2019 | Larocca et al. |
| 10,240,127 B2 | 3/2019 | Larocca et al. |
| 2001/0039316 A1 | 11/2001 | Campbell et al. |
| 2002/0001842 A1 | 1/2002 | Chapman |
| 2002/0051762 A1 | 5/2002 | Rafii et al. |
| 2002/0069484 A1 | 6/2002 | Creel |
| 2002/0142397 A1 | 10/2002 | Collas et al. |
| 2003/0046722 A1 | 3/2003 | Collas et al. |
| 2003/0129745 A1 | 7/2003 | Robl et al. |
| 2003/0149277 A1 | 8/2003 | Gaster et al. |
| 2003/0161817 A1 | 8/2003 | Young et al. |
| 2003/0166633 A1 | 9/2003 | Gaster et al. |
| 2003/0180268 A1 | 9/2003 | Atala |
| 2003/0232430 A1 | 12/2003 | Cibelli et al. |
| 2004/0001807 A1 | 1/2004 | Edelberg et al. |
| 2004/0039198 A1 | 2/2004 | Bender et al. |
| 2004/0063745 A1 | 4/2004 | Gellibert et al. |
| 2004/0152738 A1 | 8/2004 | Gaster et al. |
| 2004/0199935 A1 | 10/2004 | Chapman |
| 2004/0219563 A1 | 11/2004 | West et al. |
| 2004/0220230 A1 | 11/2004 | Gaster et al. |
| 2004/0228847 A1 | 11/2004 | Goldschmidt-Clermont et al. |

(Continued)

FOREIGN PATENT DOCUMENTS

| | | |
|---|---|---|
| EP | 1001806 A1 | 5/2000 |
| EP | 1523990 A1 | 4/2005 |

(Continued)

OTHER PUBLICATIONS

Ferrari et al., Transforming Growth Factor-Beta 1 (TGF-β1) Induces Angiogenesis Through Vascular Endothelial Growth Factor (VEGF)—Mediated Apoptosis, Journal of Cellular Physiology, vol. 219:pp. 449-458, 2009.*
Wong et al., Pharmacology & Therapeutics 151 (2015) 107-120 (Year: 2015).*
Crisan et al, Cell Stem Cell, 2008, vol. 3, pp. 301-313. (Year: 2008).*
Armulik, A. et al., "Pericytes regulate the blood-brain barrier," Nature, 468(7323), 2010, 557-61.
Armulik, A. et al., "Pericytes: developmental, physiological, and pathological perspectives, problems, and promises", Dev. Cell 21(2), 2011, 193-215.
Bergers, G. et al., "The role of pericytes in blood-vessel formation and maintenance", Neuro-Oncol. 7(4), 2005, 452-64.
Birbrair, A. et al., "Role of pericytes in skeletal muscle regeneration and fat accumulation", Stem Cells Dev. 22(16), 2013, 2298-314.

(Continued)

*Primary Examiner* — Allison M Fox
(74) *Attorney, Agent, or Firm* — McCarter & English, LLP; Jonathan M. Sparks

(57) ABSTRACT

The invention provides methods, compositions and kits for making and using pericyte-like cells or perivascular stromal cells derived from pPS cells.

8 Claims, 10 Drawing Sheets

(56) References Cited

U.S. PATENT DOCUMENTS

| | | |
|---|---|---|
| 2004/0266842 A1 | 12/2004 | Gaster et al. |
| 2005/0014258 A1 | 1/2005 | Collas et al. |
| 2005/0014938 A1 | 1/2005 | Gaster et al. |
| 2005/0165011 A1 | 7/2005 | Gellibert et al. |
| 2005/0250727 A1 | 11/2005 | Tasken et al. |
| 2006/0003446 A1 | 1/2006 | Keller et al. |
| 2006/0212952 A1 | 9/2006 | Collas et al. |
| 2007/0072901 A1 | 3/2007 | Washio |
| 2007/0116684 A1 | 5/2007 | Atala et al. |
| 2007/0154428 A1 | 7/2007 | Sato et al. |
| 2007/0155013 A1 | 7/2007 | Akaike et al. |
| 2008/0070303 A1 | 3/2008 | West et al. |
| 2008/0233610 A1 | 9/2008 | Thomson |
| 2009/0047263 A1 | 2/2009 | Yamanaka |
| 2009/0104159 A1 | 4/2009 | Prosper et al. |
| 2009/0148423 A1 | 6/2009 | Sumitran-Holgersson |
| 2009/0269314 A1 | 10/2009 | Keller et al. |
| 2010/0003757 A1 | 1/2010 | Mack |
| 2010/0055678 A1 | 3/2010 | Jaatinen et al. |
| 2010/0111914 A1* | 5/2010 | Zhang .............. A61K 35/22 424/93.21 |
| 2010/0158872 A1 | 6/2010 | Keller et al. |
| 2010/0166713 A1 | 7/2010 | Dalton et al. |
| 2010/0167404 A1 | 7/2010 | West et al. |
| 2010/0183620 A1 | 7/2010 | Bhawe et al. |
| 2010/0184033 A1 | 7/2010 | West et al. |
| 2010/0203021 A1 | 8/2010 | Goumans et al. |
| 2010/0255580 A1 | 10/2010 | Rezania |
| 2010/0267135 A1 | 10/2010 | Sakurada et al. |
| 2011/0064701 A1 | 3/2011 | Young et al. |
| 2011/0218143 A1 | 9/2011 | Kaushal et al. |
| 2011/0223669 A1 | 9/2011 | Yamanaka et al. |
| 2012/0060232 A1 | 3/2012 | Stan |
| 2012/0093885 A1 | 4/2012 | Sahoo et al. |
| 2012/0148546 A1* | 6/2012 | Dar-Oaknin ......... C12N 5/0692 424/93.7 |
| 2012/0171171 A1 | 7/2012 | West et al. |
| 2012/0295347 A1 | 11/2012 | Kessler |
| 2012/0301443 A1 | 11/2012 | Raffi et al. |
| 2013/0115673 A1 | 5/2013 | West et al. |
| 2013/0196865 A1 | 8/2013 | Hochedlinger et al. |
| 2013/0202564 A1 | 8/2013 | Han et al. |
| 2013/0236961 A1 | 9/2013 | Amit et al. |
| 2014/0010801 A1 | 1/2014 | Niedernhofer et al. |
| 2014/0178988 A1 | 6/2014 | West et al. |
| 2015/0275177 A1 | 10/2015 | West et al. |
| 2016/0002597 A1 | 1/2016 | Sinden et al. |
| 2016/0186170 A1 | 6/2016 | West et al. |
| 2016/0193252 A1 | 7/2016 | Hicks et al. |
| 2017/0108503 A1 | 4/2017 | Klass et al. |
| 2017/0146529 A1 | 5/2017 | Nagrath et al. |
| 2019/0151372 A1 | 5/2019 | Larocca et al. |
| 2019/0175691 A1 | 6/2019 | West et al. |
| 2019/0218511 A1 | 7/2019 | Larocca et al. |
| 2019/0241873 A1 | 8/2019 | Larocca et al. |

FOREIGN PATENT DOCUMENTS

| | | | |
|---|---|---|---|
| EP | | 1860180 A1 | 11/2007 |
| EP | | 2254586 A1 | 12/2010 |
| EP | | 2496711 A2 | 9/2012 |
| JP | | 2016-518393 A | 6/2016 |
| WO | WO-1998/30679 A1 | | 7/1998 |
| WO | WO-1999/003499 A1 | | 1/1999 |
| WO | WO-1999/20741 A1 | | 4/1999 |
| WO | WO-2001/00650 A1 | | 1/2001 |
| WO | WO-2001/30978 A1 | | 5/2001 |
| WO | WO-2001/51616 A2 | | 7/2001 |
| WO | WO-2003/046141 A2 | | 6/2003 |
| WO | WO-2003/074654 A2 | | 9/2003 |
| WO | WO-2003/076603 A2 | | 9/2003 |
| WO | WO-2005/068610 A1 | | 7/2005 |
| WO | WO-2005/121369 A2 | | 12/2005 |
| WO | WO-2006/130504 A2 | | 12/2006 |
| WO | WO-2007/019398 A1 | | 2/2007 |
| WO | WO-2007/047894 A2 | | 4/2007 |
| WO | WO-2007/058671 A1 | | 5/2007 |
| WO | WO-2008/089448 A2 | | 7/2008 |
| WO | WO-2008/148938 A1 | | 12/2008 |
| WO | WO-2009/052211 A1 | | 4/2009 |
| WO | WO-2009/105044 A1 | | 8/2009 |
| WO | WO-2010/021993 A1 | | 2/2010 |
| WO | WO-2011/053257 A2 | | 5/2011 |
| WO | WO-2011/150105 A2 | | 12/2011 |
| WO | WO-2012/020308 A2 | | 2/2012 |
| WO | WO-2012/125471 A1 | | 9/2012 |
| WO | WO-2013/003595 A1 | | 1/2013 |
| WO | WO-2013/014691 A1 | | 1/2013 |
| WO | WO-2013/036969 A1 | | 3/2013 |
| WO | WO-2013/150303 A1 | | 10/2013 |
| WO | WO-2013/172793 A1 | | 11/2013 |
| WO | WO-2014/013258 A1 | | 1/2014 |
| WO | WO-2014/022852 A1 | | 2/2014 |
| WO | WO-2014/028493 A2 | | 2/2014 |
| WO | WO-2014/091373 A1 | | 6/2014 |
| WO | WO-2014/125276 A1 | | 8/2014 |
| WO | WO-2014/125277 A1 | | 8/2014 |
| WO | WO-2014/197421 A1 | | 12/2014 |
| WO | WO-2015/052526 A1 | | 4/2015 |
| WO | WO-2015/052527 A1 | | 4/2015 |

OTHER PUBLICATIONS

Birbrair, A. et al., "Type-2 pericytes participate in normal and tumoral angiogenesis", Am J Physiol Cell Physiol. 307(1), 2014, C25-38.

Blocki, A. et al., "Not All MSCs Can Act as Pericytes: Functional In Vitro Assays to Distinguish Pericytes from Other Mesenchymal Stem Cells in Angiogenesis," Stem Cells Dev. 22(17):2347-2355 (2013).

Chen, C.W. et al., "Human pericytes for ischemic heart repair," Stem Cells 31:305-316 (2013).

Chen, C.W. et al., "Human Myocardial Pericytes: Multipotent Mesodermal Precursors Exhibiting Cardiac Specificity," Stem Cells 33:557-573 (2015).

Chen, S.T. et al., "A model of focal ischemic stroke in the rat: reproducible extensive cortical infarction", Stroke. 17(4), 1986, 738-43.

Corselli, M. et al., "Identification of perivascular mesenchymal stromal/stem cells by flow cytometry", Cytometry A. 83(8), 2013, 714-20.

Daneman, R. et al., "Pericytes are required for blood-brain barrier integrity during embryogenesis", Nature. 468(7323), 2010, 562-566.

Dar, A. et al., "Multipotent vasculogenic pericytes from human pluripotent stem cells promote recovery of murine ischemic limb", Circulation. 125(1), 2012, 87-99.

Dore-Duffy, P. et al., "Morphology and properties of pericytes", Methods Mol Biol. 686, 2011, 49-68.

Elali, A. et al., "The role of pericytes in neurovascular unit remodeling in brain disorders", Int. J. Mol. Sci. 15(4), 2014, 6453-6474.

Fu, J. et al., "Endothelial cell O-glycan deficiency causes blood/lymphatic misconnections and consequent fatty liver disease in mice", J. Olin. Invest. 118(11), 2008, 3725-3737.

Garbuzova-Davis, S. et al., "Blood-CNS Barrier Impairment in ALS patients versus an animal model", Front. Cell. Neurosci. 8: 2014, p. 1-9.

James, A. et al., "An Abundant Perivascular Source of Stem Cells for Bone Tissue Engineering," Stem Cells Translational Medicine 1:673-684 (2012).

James, D. et al., "Expansion and maintenance of human embryonic stem cell-derived endothelial cells by TGFβ inhibition is Id1 dependent," Nat Biotechnol. 28(2):161-166 (2010).

Lai, A.K. et al., "Animal models of diabetic retinopathy: summary and comparison", J Diabetes Res. 2013, 2013, 106594, p. 1-29.

Limbourg, A. et al., "Evaluation of postnatal arteriogenesis and angiogenesis in a mouse model of hind-limb ischemia", Nat Protoc. 4(12), 2009, 1737-46.

(56) References Cited

OTHER PUBLICATIONS

Odaka, C., "Localization of mesenchymal cells in adult mouse thymus: their abnormal distribution in mice with disorganization of thymic medullary epithelium", J. Histochem. Cytochem. 2009, 57(4), 2009, 373-382.

Orlova, V.V. et al., "Functionality of endothelial cells and pericytes from human pluripotent stem cells demonstrated in cultured vascular plexus and zebrafish xenografts", Arterioscler Thromb. Vasc. Biol. 34(1), 2014, 177-186.

Ragni, E. et al., "Adipogenic potential in human mesenchymal stem cells strictly depends on adult or foetal tissue harvest," Int J Biochem Cell Biol. 45(11):2456-2466 (2013).

Sagare, A.P. et al., "Pericyte loss influences Alzheimer-like neurodegeneration in mice", Nat. Commun. 4:2932 (2013), p. 1-14.

Wanjare, M., et al., "Defining Differences among Perivascular Cells Derived from Human Pluripotent Stem Cells," Stem Cell Reports 2:561-575 (2014).

West, et al., "The ACTCellerate initiative: large-scale combinatorial cloning of novel human embryonic stem cell derivatives", Regen. Med. 3(3):287-308 (2008).

Wilcock, D.M. et al., "Vascular amyloid alters astrocytic water and potassium channels in mouse models and humans with Alzheimer's disease", Neuroscience 159(3):1055-1069 (2009).

Winkler, E.A. et al., "Blood-spinal cord barrier breakdown and pericyte reductions in amyotrophic lateral sclerosis", Acta Neuropathol. 125(1): 111-120 (2013).

Yemisci, M. et al., "Pericyte contraction induced by oxidative-nitrative stress impairs capillary reflow despite successful opening of an occluded cerebral artery", Nat. Med. 15(9): 1031-1038 (2009).

Zaragoza, C. , "Animal models of cardiovascular diseases", J Biomed Biotechnol. 2011, 2011, 497841.

Amieux et al., Cyclic nucleotides converge on brown adipose tissue differentiation. Sci Signal. Jan. 12, 2010;3(104):pe2. 3 pages.

Bai et al., BMP4 regulates vascular progenitor development in human embryonic stem cells through a Smad-dependent pathway. J Cell Biochem. Feb. 1, 2010;109(2):363-74.

Beranger et al., In vitro brown and "brite"/"beige" adipogenesis: human cellular models and molecular aspects. Biochim Biophys Acta. May 2013;1831(5):905-14.

Bian et al., Extracellular vesicles derived from human bone marrow mesenchymal stem cells promote angiogenesis in a rat myocardial infarction model. J Mol Med (Berl). Apr. 2014;92(4):387-97.

Bignone et al., Identification of human embryonic progenitor cell targeting peptides using phage display. PLoS One. 2013;8(3):e58200. 12 pages.

Blanpain et al., Stem cells assessed. Nat Rev Mol Cell Biol. Jun. 8, 2012;13(7):471-6.

Bloom et al., Disodium (R,R)-5-[2[[2-(3-chlorophenyl)-2-hydroxyethyl]-amino] propyl]-1,3-benzodioxole-2,2-dicarboxylate (CL 316,243). A potent beta-adrenergic agonist virtually specific for beta 3 receptors. A promising antidiabetic and antiobesity agent. J Med Chem. Aug. 7, 1992;35(16):3081-4.

Blum et al., The tumorigenicity of diploid and aneuploid human pluripotent stem cells. Cell Cycle. Dec. 2009;8(23):3822-30.

Bogos et al., VEGFR-3-positive circulating lymphatic/vascular endothelial progenitor cell level is associated with poor prognosis in human small cell lung cancer. Clin Cancer Res. Mar. 1, 2009;15(5):1741-6.

Bongso et al., Improved quality of human embryos when co-cultured with human ampullary cells. Hum Reprod. Aug. 1989;4(6):706-13.

Bongso et al., Isolation and culture of inner cell mass cells from human blastocysts. Hum Reprod. Nov. 1994;9(11):2110-7.

Bruno et al., Mesenchymal stem cell-derived microvesicles protect against acute tubular injury. J Am Soc Nephrol. May 2009;20(5):1053-67.

Camussi et al., Exosomes/microvesicles as a mechanism of cell-to-cell communication. Kidney Int. Nov. 2010;78(9):838-48.

Cannon et al., Brown adipose tissue: function and physiological significance. Physiol Rev. Jan. 2004;84(1):277-359.

Cannon et al., Cultures of adipose precursor cells from brown adipose tissue and of clonal brown-adipocyte-like cell lines. Methods Mol Biol. 2001;155:213-24.

Carmeliet, Angiogenesis in life, disease and medicine. Nature. Dec. 15, 2005;438(7070):932-6.

Cheema et al., Regulation and guidance of cell behavior for tissue regeneration via the siRNA mechanism. Wound Repair Regen. May-Jun. 2007;15(3):286-95.

Chen et al., Enabling a robust scalable manufacturing process for therapeutic exosomes through oncogenic immortalization of human ESC-derived MSCs. J Transl Med. Apr. 25, 2011;9:47. 10 pages.

Chung et al., Human embryonic stem cell lines generated without embryo destruction. Cell Stem Cell. Feb. 7, 2008;2(2):113-7.

Cibelli et al., Transgenic bovine chimeric offspring produced from somatic cell-derived stem-like cells. Nat Biotechnol. Jul. 1998;16(7):642-6.

Climent et al., TGFbeta Triggers miR-143/145 Transfer From Smooth Muscle Cells to Endothelial Cells, Thereby Modulating Vessel Stabilization. Circ Res. May 22, 2015;116(I1):1753-64.

Cohen et al., Turning straw into gold: directing cell fate for regenerative medicine. Nat Rev Genet. Apr. 2011;12(4):243-52.

Conley et al., BMPs regulate differentiation of a putative visceral endoderm layer within human embryonic stem-cell-derived embryoid bodies. Biochem Cell Biol. Feb. 2007;85(1):121-32.

Cooper et al., Modulation of PGC-1 coactivator pathways in brown fat differentiation through LRP130. J Biol Chem. Nov. 14, 2008;283(46):31960-7.

Costa et al., The hESC line Envy expresses high levels of GFP in all differentiated progeny. Nat Methods. Apr. 2005;2(4):259-60.

Crook et al., The generation of six clinical-grade human embryonic stem cell lines. Cell Stem Cell. Nov. 2007;1(5):490-4.

Dai et al., MicroRNA-223-3p inhibits the angiogenesis of ischemic cardiac microvascular endothelial cells via affecting RPS6KB1/hif-la signal pathway. PLoS One. Oct. 14, 2014;9(10):e108468. 14 pages.

De Souza Batista et al., Omentin plasma levels and gene expression are decreased in obesity. Diabetes. Jun. 2007;56(6):1655-61.

Dechesne et al., Stem Cells from Human Adipose Tissue: A New Tool for Pharmacological Studies and for Clinical Applications. Adipose Stem Cells and Regenerative Medicine. Y.-G. Illouz (Ed.), Springer-Verlag Berlin Heidelberg. Chapter 12, pp. 121-132, (2011).

Deregibus et al., Endothelial progenitor cell derived microvesicles activate an angiogenic program in endothelial cells by a horizontal transfer of mRNA. Blood. Oct. 1, 2007;110(7):2440-8.

Desandro et al., Associations and interactions between bare lymphocyte syndrome factors. Mol Cell Biol. Sep. 2000;20(17):6587-99.

Dubois et al., SIRPA is a specific cell-surface marker for isolating cardiomyocytes derived from human pluripotent stem cells. Nat Biotechnol. Oct. 23, 2011;29(11):1011-8.

Durick et al., Hunting with traps: genome-wide strategies for gene discovery and functional analysis. Genome Res. Nov. 1999;9(11):1019-25.

Díez et al., Endothelial progenitor cells undergo an endothelial-to-mesenchymal transition-like process mediated by TGFbetaRI. Cardiovasc Res. Dec. 1, 2010;88(3):502-11.

Elabd et al., Human multipotent adipose-derived stem cells differentiate into functional brown adipocytes. Stem Cells. Nov. 2009;27(11):2753-60.

Espandar et al., Adipose-derived stem cells on hyaluronic acid-derived scaffold: a new horizon in bioengineered cornea. Arch Ophthalmol. Feb. 2012;130(2):202-8.

Fedorenko et al., Mechanism of fatty-acid-dependent UCP1 uncoupling in brown fat mitochondria. Cell. Oct. 12, 2012;151(2):400-13.

Fish et al., miR-126 regulates angiogenic signaling and vascular integrity. Dev Cell. Aug. 2008;15(2):272-84.

Follenzi et al., Gene transfer by lentiviral vectors is limited by nuclear translocation and rescued by HIV-1 pol sequences. Nat Genet. Jun. 2000;25(2):217-22.

Forte et al., MicroRNA-mediated transformation by the Kaposi's sarcoma-associated herpesvirus Kaposin locus. J Virol. Feb. 2015;89(4):2333-41.

(56) References Cited

OTHER PUBLICATIONS

Francavilla et al., Transient GFER knockdown in vivo impairs liver regeneration after partial hepatectomy. Int J Biochem Cell Biol. Aug. 2014;53:343-51.
Funk et al., Evaluating the genomic and sequence integrity of human ES cell lines; comparison to normal genomes. Stem Cell Res. Mar. 2012;8(2):154-64.
Gao et al., Endothelial progenitor cells control the angiogenic switch in mouse lung metastasis. Science. Jan. 11, 2008;319(5860):195-8.
Garcia et al., Glucose Starvation in Cardiomyocytes Enhances Exosome Secretion and Promotes Angiogenesis in Endothelial Cells. PLoS One. Sep. 22, 2015;10(9):e0138849. 23 pages.
Gardner et al., Culture and transfer of human blastocysts increases implantation rates and reduces the need for multiple embryo transfers. Fertil Steril. Jan. 1998;69(1):84-8.
Gehling et al., In vitro differentiation of endothelial cells from AC133-positive progenitor cells. Blood. May 15, 2000;95(10):3106-12.
George et al., Isolation of human platelet membrane microparticles from plasma and serum. Blood. Oct. 1982;60(4):834-40.
Goldman et al., A boost of BMP4 accelerates the commitment of human embryonic stem cells to the endothelial lineage. Stem Cells. Aug. 2009;27(8):1750-9.
Golozoubova et al., Only UCP1 can mediate adaptive nonshivering thermogenesis in the cold. FASEB J. Sep. 2001;15(11):2048-50.
Goumans et al., TGF-beta signaling in vascular biology and dysfunction. Cell Res. Jan. 2009;19(1):116-27.
Grigolo et al., Transplantation of chondrocytes seeded on a hyaluronan derivative (hyaff-11) into cartilage defects in rabbits. Biomaterials. Sep. 2001;22(17):2417-24.
Grützkau et al., Small but mighty: how the MACS-technology based on nanosized superparamagnetic particles has helped to analyze the immune system within the last 20 years. Cytometry A. Jul. 2010;77(7):643-7.
Guduric-Fuchs et al., Selective extracellular vesicle-mediated export of an overlapping set of microRNAs from multiple cell types. BMC Genomics. Aug. 1, 2012;13:357. 14 pages.
Haflidadóttir et al., Upregulation of miR-96 enhances cellular proliferation of prostate cancer cells through FOXO1. PLoS One. Aug. 12, 2013;8(8):e72400. 11 pages.
Harms et al., Brown and beige fat: development, function and therapeutic potential. Nat Med. Oct. 2013;19(10):1252-63.
Hassan et al., Encapsulation and 3D culture of human adipose-derived stem cells in an in-situ crosslinked hybrid hydrogel composed of PEG-based hyperbranched copolymer and hyaluronic acid. Stem Cell Res Ther. Mar. 21, 2013;4(2):32. 11 pages.
Hedman et al., Isolation of the pericellular matrix of human fibroblast cultures. J Cell Biol. Apr. 1979;81(1):83-91.
Hemmrich et al., Implantation of preadipocyte-loaded hyaluronic acid-based scaffolds into nude mice to evaluate potential for soft tissue engineering. Biomaterials. Dec. 2005;26(34):7025-37.
Herrera et al., Human liver stem cell-derived microvesicles accelerate hepatic regeneration in hepatectomized rats. J Cell Mol Med. Jun. 2010;14(6B):1605-18.
Ho et al., Synthetic protein transduction domains: enhanced transduction potential in vitro and in vivo. Cancer Res. Jan. 15, 2001;61(2):474-7.
Honda et al., Cartilage formation by cultured chondrocytes in a new scaffold made of poly(L-lactide-epsilon-caprolactone) sponge. J Oral Maxillofac Surg. Jul. 2000;58(7):767-75.
Huber et al., Haemangioblast commitment is initiated in the primitive streak of the mouse embryo. Nature. Dec. 2, 2004;432(7017):625-30.
Hynes et al., Micropatterning of 3D Microenvironments for Living Biosensor Applications. Biosensors (Basel). Mar. 2014;4(1):28-44.
Hölig et al., Novel RGD lipopeptides for the targeting of liposomes to integrin-expressing endothelial and melanoma cells. Protein Eng Des Sel. May 2004;17(5):433-41.
Hüttemann et al., Mice deleted for heart-type cytochrome c oxidase subunit 7a1 develop dilated cardiomyopathy. Mitochondrion. Mar. 2012;12(2):294-304.
Ibrahim et al., Exosomes as critical agents of cardiac regeneration triggered by cell therapy. Stem Cell Reports. May 8, 2014;2(5):606-19.
Inman et al., SB-431542 is a potent and specific inhibitor of transforming growth factor-beta superfamily type I activin receptor-like kinase (ALK) receptors ALK4, ALK5, and ALK7. Mol Pharmacol. Jul. 2002;62(1):65-74.
Jackson et al., Recognizing and avoiding siRNA off-target effects for target identification and therapeutic application. Nat Rev Drug Discov. Jan. 2010;9(1):57-67.
Jaiswal et al., Long-term multiple color imaging of live cells using quantum dot bioconjugates. Nat Biotechnol. Jan. 2003;21(1):47-51.
Jakob et al., Role of microRNAs in stem/progenitor cells and cardiovascular repair. Cardiovasc Res. Mar. 15, 2012;93(4):614-22.
James et al., Contribution of human embryonic stem cells to mouse blastocysts. Dev Biol. Jul. 1, 2006;295(1):90-102.
Jankovic et al., Id1 restrains myeloid commitment, maintaining the self-renewal capacity of hematopoietic stem cells. Proc Natl Acad Sci USA. Jan. 23, 2007;104(4):1260-5.
Jeong et al., Nanovesicles engineered from ES cells for enhanced cell proliferation. Biomaterials. Nov. 2014;35(34):9302-10.
Kane et al., Derivation of endothelial cells from human embryonic stem cells by directed differentiation: analysis of microRNA and angiogenesis in vitro and in vivo. Arterioscler Thromb Vasc Biol. Jul. 2010;30(7):1389-97.
Kang et al., A self-enabling TGFbeta response coupled to stress signaling: Smad engages stress response factor ATF3 for Id1 repression in epithelial cells. Mol Cell. Apr. 2003;11(4):915-26.
Karamanlidis et al., C/EBPbeta reprograms white 3T3-L1 preadipocytes to a Brown adipocyte pattern of gene expression. J Biol Chem. Aug. 24, 2007;282(34):24660-9.
Kawamoto et al., Role of progenitor endothelial cells in cardiovascular disease and upcoming therapies. Catheter Cardiovasc Interv. Oct. 1, 2007;70(4):477-84.
Kazantzis et al., PAZ6 cells constitute a representative model for human brown pre-adipocytes. Front Endocrinol (Lausanne). Feb. 2, 2012;3:13.
Keller et al., Exosomes: from biogenesis and secretion to biological function. Immunol Lett. Nov. 15, 2006;107(2):102-8.
Kelly et al., Signaling hierarchy regulating human endothelial cell development. Arterioscler Thromb Vasc Biol. May 2009;29(5):718-24.
Khakoo et al., Endothelial progenitor cells. Annu Rev Med. 2005;56:79-101.
Kim et al., Extracellular membrane vesicles from tumor cells promote angiogenesis via sphingomyelin. Cancer Res. Nov. 1, 2002;62(21):6312-7.
King et al., Hypoxic enhancement of exosome release by breast cancer cells. BMC Cancer. Sep. 24, 2012;12:421. 10 pages.
Korchagin, Neoplastic Diseases Reviews, Stem Cells. CancerLink.ru. 26 pages, (2011).
Krosl et al., In vitro expansion of hematopoietic stem cells by recombinant TAT-HOXB4 protein. Nat Med. Nov. 2003;9(11):1428-32.
Kucharzewska et al., Exosomes reflect the hypoxic status of glioma cells and mediate hypoxia-dependent activation of vascular cells during tumor development. PNAS. Apr. 30, 2013;110(18):7312-7317.
Laine et al., MicroRNAs miR-96, miR-124, and miR-199a egulate gene expression in human bone marrow-derived mesenchymal stem cells. J Cell Biochem. Aug. 2012;113(8):2687-95.
Lanza et al., Human therapeutic cloning. Nat Med. Sep. 1999;5(9):975-7.
Laping et al., Inhibition of transforming growth factor (TGF)-beta1-induced extracellular matrix with a novel inhibitor of the TGF-beta type I receptor kinase activity: SB-431542. Mol Pharmacol. Jul. 2002;62(1):58-64.
Laposa, Stem cells for drug screening. J Cardiovasc Pharmacol. Sep. 2011;58(3):240-5.

(56) References Cited

OTHER PUBLICATIONS

Le Grand et al., Six1 regulates stem cell repair potential and self-renewal during skeletal muscle regeneration. J Cell Biol. Sep. 3, 2012;198(5):815-32.
Lee et al., Deletion of heart-type cytochrome c oxidase subunit 7a1 impairs skeletal muscle angiogenesis and oxidative phosphorylation. J Physiol. Oct. 15, 2012;590(20):5231-43.
Lee et al., Exosomes mediate the cytoprotective action of mesenchymal stromal cells on hypoxia-induced pulmonary hypertension. Circulation. Nov. 27, 2012;126(22):2601-11.
Lee et al., HLA-E is a major ligand for the natural killer inhibitory receptor CD94/NKG2A. Proc Natl Acad Sci U S A. Apr. 28, 1998;95(9):5199-204.
Levenberg et al., Endothelial cells derived from human embryonic stem cells. Proc Natl Acad Sci U S A. Apr. 2, 2002;99(7):4391-6.
Levenberg et al., Endothelial potential of human embryonic stem cells. Blood. Aug. 1, 2007;110(3):806-14.
Li et al., Comparison of reporter gene and iron particle labeling for tracking fate of human embryonic stem cells and differentiated endothelial cells in living subjects. Stem Cells. Apr. 2008;26(4):864-73.
Lin et al., Quantum dot imaging for embryonic stem cells. BMC Biotechnol. Oct. 9, 2007;7:67. 10 pages.
Lin et al., Unregulated miR-96 induces cell proliferation in human breast cancer by downregulating transcriptional factor FOXO3a. PLoS One. Dec. 23, 2010;5(12):e15797. 10 pages.
Liu et al., MiR-106b and MiR-15b modulate apoptosis and angiogenesis in myocardial infarction. Cell Physiol Biochem. 2012;29(5-6):851-62.
Lopatina et al., Platelet-derived growth factor regulates the secretion of extracellular vesicles by adipose mesenchymal stem cells and enhances their angiogenic potential. Cell Commun Signal. Apr. 11, 2014;12:26. 12 pages.
Lu et al., Generation of functional hemangioblasts from human embryonic stem cells. Nat Methods. Jun. 2007;4(6):501-9.
Lu et al., Targeting of embryonic stem cells by peptide-conjugated quantum dots. PLoS One. Aug. 10, 2010;5(8):e12075. 10 pages.
Lyden et al., Impaired recruitment of bone-marrow-derived endothelial and hematopoietic precursor cells blocks tumor angiogenesis and growth. Nat Med. Nov. 2001;7(11):1194-201.
Mali et al., Improved efficiency and pace of generating induced pluripotent stem cells from human adult and fetal fibroblasts. Stem Cells. Aug. 2008;26(8):1998-2005.
Martinez et al., Shed membrane microparticles from circulating and vascular cells in regulating vascular function. Am J Physiol Heart Circ Physiol. Mar. 2005;288(3):H1004-9.
Molek et al., Peptide phage display as a tool for drug discovery: targeting membrane receptors. Molecules. Jan. 21, 2011;16(1):857-87.
Nakagawa et al., Reprogramming of somatic cells to pluripotency. Adv Exp Med Biol. 2010;695:215-24.
Nakashiba et al., Netrin-G1: a novel glycosyl phosphatidylinositol-linked mammalian netrin that is functionally divergent from classical netrins. J Neurosci. Sep. 1, 2000;20(17):6540-50.
Naldini et al., In vivo gene delivery and stable transduction of nondividing cells by a lentiviral vector. Science. Apr. 12, 1996;272(5259):263-7.
Nelson et al., Induced pluripotent stem cells: advances to applications. Stem Cells Cloning. Jan. 1, 2010;3:29-37.
Nicoli et al., MicroRNA-mediated integration of haemodynamics and Vegf signalling during angiogenesis. Nature. Apr. 22, 2010;464(7292):1196-200.
Niemelä et al., Molecular identification of PAL-E, a widely used endothelial-cell marker. Blood. Nov. 15, 2005;106(10):3405-9.
Nonaka et al., Development of stabilin2+ endothelial cells from mouse embryonic stem cells by inhibition of TGFbeta/activin signaling. Biochem Biophys Res Commun. Oct. 17, 2008;375(2):256-60.
Nourse et al., VEGF induces differentiation of functional endothelium from human embryonic stem cells: implications for tissue engineering. Arterioscler Thromb Vasc Biol. Jan. 2010;30(1):80-9.
Ohshima et al., Let-7 microRNA family is selectively secreted into the extracellular environment via exosomes in a metastatic gastric cancer cell line. PLoS One. Oct. 8, 2010;5(10):e13247. 10 pages.
Ong et al., Cross talk of combined gene and cell therapy in ischemic heart disease: role of exosomal microRNA transfer. Circulation. Sep. 9, 2014;130(11 Suppl 1):560-9.
Pankratz et al., MicroRNA-155 Exerts Cell-Specific Antiangiogenic but Proarteriogenic Effects During Adaptive Neovascularization. Circulation. May 5, 2015;131(18):1575-89.
Patel et al., Poly(ethylene glycol) hydrogel system supports preadipocyte viability, adhesion, and proliferation. Tissue Eng. Sep.-Oct. 2005;11(9-10):1498-505.
Peichev et al., Expression of VEGFR-2 and AC133 by circulating human CD34(+) cells identifies a population of functional endothelial precursors. Blood. Feb. 1, 2000;95(3):952-8.
Perka et al., Joint cartilage repair with transplantation of embryonic chondrocytes embedded in collagen-fibrin matrices. Clin Exp Rheumatol. Jan.-Feb. 2000;18(1):13-22.
Prestwich et al., The translational imperative: making cell therapy simple and effective. Acta Biomater. Dec. 2012;8(12):4200-7.
Rafii et al., Cancer. A few to flip the angiogenic switch. Science. Jan. 11, 2008;319(5860):1634.
Rasmussen et al., TNFerade Biologic: preclinical toxicology of a novel adenovector with a radiation-inducible promoter, carrying the human tumor necrosis factor alpha gene. Cancer Gene Ther. Nov. 2002;9(11):951-7.
Religa et al., Presence of bone marrow-derived circulating progenitor endothelial cells in the newly formed lymphatic vessels. Blood. Dec. 15, 2005;106(13):4184-90.
Reubinoff et al., Embryonic stem cell lines from human blastocysts: somatic differentiation in vitro. Nat Biotechnol. Apr. 2000;18(4):399-404.
Rhie et al., Implantation of Cultured Preadipocyte Using Chitosan/Alginate Sponge. Key Engineering Materials. 2007;342-343;349-352.
Riolobos et al., HLA engineering of human pluripotent stem cells. Mol Ther. Jun. 2013;21(6):1232-41.
Rong et al., A scalable approach to prevent teratoma formation of human embryonic stem cells. J Biol Chem. Sep. 21, 2012;287(39):32338-45.
Rong et al., An effective approach to prevent immune rejection of human ESC-derived allografts. Cell Stem Cell. Jan. 2, 2014;14(1):121-30.
Rosensteel et al., COL1A1 oligodeoxynucleotides decoy: biochemical and morphologic effects in an acute wound repair model. Exp Mol Pathol. Dec. 2010;89(3):307-13.
Rosler et al., Long-term culture of human embryonic stem cells in feeder-free conditions. Dev Dyn. Feb. 2004;229(2):259-74.
Rossig et al., Histone deacetylase activity is essential for the expression of HoxA9 and for endothelial commitment of progenitor cells. J Exp Med. Jun. 6, 2005;201(11):1825-35.
Rudert et al., Bioartificial Cartilage. Cells Tissues Organs. 2000;167:95-105.
Ruzinova et al., Id proteins in development, cell cycle and cancer. Trends Cell Biol. Aug. 2003;13(8):410-8.
Sahoo et al., Exosomes from human CD34(+) stem cells mediate their proangiogenic paracrine activity. Circ Res. Sep. 16, 2011;109(7):724-8.
Salven et al., VEGFR-3 and CD133 identify a population of CD34+ lymphatic/vascular endothelial precursor cells. Blood. Jan. 1, 2003;101(1):168-72.
Schnerch et al., Distinguishing between mouse and human pluripotent stem cell regulation: the best laid plans of mice and men. Stem Cells. Mar. 31, 2010;28(3):419-30.
Schniedermann et al., Mouse lung contains endothelial progenitors with high capacity to form blood and lymphatic vessels. BMC Cell Biology. 2010;11(50):1-13.
Schulz et al., Identification of inducible brown adipocyte progenitors residing in skeletal muscle and white fat. Proc Natl Acad Sci U S A. Jan. 4, 2011;108(1):143-8.

(56) References Cited

OTHER PUBLICATIONS

Schwarze et al., In vivo protein transduction: intracellular delivery of biologically active proteins, compounds and DNA. Trends Pharmacol Sci. Feb. 2000;21(2):45-8.
Scott et al., Current methods of adipogenic differentiation of mesenchymal stem cells. Stem Cells Dev. Oct. 2011;20(10):1793-804.
Seale et al., PRDM16 controls a brown fat/skeletal muscle switch. Nature. Aug. 21, 2008;454(7207):961-7.
Seandel et al., Generation of a functional and durable vascular niche by the adenoviral E4ORF1 gene. Proc Natl Acad Sci U S A. Dec. 9, 2008;105(49):19288-93.
Semo et al., The 106b-25 microRNA cluster is essential for neovascularization after hindlimb ischaemia in mice. Eur Heart J. Dec. 1, 2014;35(45):3212-23.
Shah et al., Labeling of mesenchymal stem cells by bioconjugated quantum dots. Nano Lett. Oct. 2007;7(10):3071-9.
Shehzad et al., Adiponectin: regulation of its production and its role in human diseases. Hormones (Athens). Jan.-Mar. 2012;11(1):8-20.
Slotkin et al., In vivo quantum dot labeling of mammalian stem and progenitor cells. Dev Dyn. Dec. 2007;236(12):3393-401.
Sobrino et al., The increase of circulating endothelial progenitor cells after acute ischemic stroke is associated with good outcome. Stroke. Oct. 2007;38(10):2759-64.
Solter et al., Immunosurgery of mouse blastocyst. Proc Natl Acad Sci U S A. Dec. 1975;72(12):5099-102.
Sone et al., Pathway for differentiation of human embryonic stem cells to vascular cell components and their potential for vascular regeneration. Arterioscler Thromb Vasc Biol. Oct. 2007;27(10):2127-34.
Song et al., Modeling disease in human ESCs using an efficient BAC-based homologous recombination system. Cell Stem Cell. Jan. 8, 2010;6(1):80-9.
Spear et al., Isolation, characterization, and recovery of small peptide phage display epitopes selected against viable malignant glioma cells. Cancer Gene Ther. Jul. 2001;8(7):506-11.
Spinetti et al., MicroRNA-15a and microRNA-16 impair human circulating proangiogenic cell functions and are increased in the proangiogenic cells and serum of patients with critical limb ischemia. Circ Res. Jan. 18, 2013;112(2):335-46.
Sternberg et al., A human embryonic stem cell-derived clonal progenitor cell line with chondrogenic potential and markers of craniofacial mesenchyme. Regen Med. Jul. 2012;7(4):481-501.
Sternberg et al., Human Embryonic Stem Cell-derived Clonal Brown Adipocyte Progenitors. BioTime, Inc. Poster Presentation. 1 page.
Stojkovic et al., An autogeneic feeder cell system that efficiently supports growth of undifferentiated human embryonic stem cells. Stem Cells. Mar. 2005;23(3):306-14.
Suzuki et al., BMPs promote proliferation and migration of endothelial cells via stimulation of VEGF-A/VEGFR2 and angiopoietin-1/Tie2 signalling. J Biochem. Feb. 2008;143(2):199-206.
Suárez et al., MicroRNAs as novel regulators of angiogenesis. Circ Res. Feb. 27, 2009;104(4):442-54.
Svensson et al., Gene expression in human brown adipose tissue. Int J Mol Med. Feb. 2011;27(2):227-32.
Tadokoro et al., Exosomes derived from hypoxic leukemia cells enhance tube formation in endothelial cells. J Biol Chem. Nov. 29, 2013;288(48):34343-51.
Takahashi et al., Induction of pluripotent stem cells from adult human fibroblasts by defined factors. Cell. Nov. 30, 2007;131(5):861-72.
Tchkonia et al., Fat depot origin affects adipogenesis in primary cultured and cloned human preadipocytes. Am J Physiol Regul Integr Comp Physiol. May 2002;282(5):R1286-96.
Tchkonia et al., Identification of depot-specific human fat cell progenitors through distinct expression profiles and development gene patterns. Am J Physiol Endocrinol Metab. 2007;292:E298-E307.
Teesalu et al., Mapping of vascular ZIP codes by phage display. Methods Enzymol. 2012;503:35-56.
Thomson et al., Embryonic stem cell lines derived from human blastocysts. Science. Nov. 6, 1998;282(5391):1145-7.
Thomson et al., Isolation of a primate embryonic stem cell line. Proc Natl Acad Sci U S A. Aug. 15, 1995;92(17):7844-8.
Thomson et al., Primate embryonic stem cells. Curr Top Dev Biol. 1998;38:133-65.
Thumser et al., Fatty acid binding proteins: tissue-specific functions in health and disease. Curr Opin Clin Nutr Metab Care. Mar. 2014;17(2):124-9.
Tiscornia et al., Diseases in a dish: modeling human genetic disorders using induced pluripotent cells. Nat Med. Dec. 2011;17(12):1570-6.
Tsuchida et al., Inhibitors of the TGF-beta superfamily and their clinical applications. Mini Rev Med Chem. Nov. 2006;6(11):1255-61.
Van Der Lans et al., Cold-activated brown adipose tissue in human adults: methodological issues. Am J Physiol Regul Integr Comp Physiol. Jul. 15, 2014;307(2):R103-13.
Wagner et al., Replicative senescence of mesenchymal stem cells: a continuous and organized process. PLoS One. May 21, 2008;3(5):e2213. 12 pages.
Wang et al., Endothelial cells derived from human embryonic stem cells form durable blood vessels in vivo. Nat Biotechnol. Mar. 2007;25(3):317-8.
Watabe et al., TGF-beta receptor kinase inhibitor enhances growth and integrity of embryonic stem cell-derived endothelial cells. J Cell Biol. Dec. 22, 2003;163(6):1303-11.
Watabe et al., TGF-beta Signaling in Embryonic Stem Cell-Derived Endothelial Cells. Methods in Molecular Biology, vol. 330: Embryonic Stem Cell Protocols, 2nd Edition: vol. 2. K. Turksen (Ed.) Humana Press Inc., Totowa, NJ. Chapter 23, pp. 341-351, (2006).
Watt et al., Human endothelial stem/progenitor cells, angiogenic factors and vascular repair. J R Soc Interface. Dec. 6, 2010;7 Suppl 6:S731-51.
Wu et al., Beige adipocytes are a distinct type of thermogenic fat cell in mouse and human. Cell. Jul. 20, 2012;150(2):366-76.
Wu et al., Molecular characterization, expression patterns and polymorphism analysis of porcine Six1 gene. Mol Biol Rep. Apr. 2011;38(4):2619-32.
Xin et al., Systemic administration of exosomes released from mesenchymal stromal cells promote functional recovery and neurovascular plasticity after stroke in rats. J Cereb Blood Flow Metab. Nov. 2013;33(11):1711-5.
Xu et al., BMP4 initiates human embryonic stem cell differentiation to trophoblast. Nat Biotechnol. Dec. 2002;20(12):1261-4.
Xu et al., Feeder-free growth of undifferentiated human embryonic stem cells. Nat Biotechnol. Oct. 2001;19(10):971-4.
Yamahara et al., Augmentation of neovascularization in hindlimb ischemia by combined transplantation of human embryonic stem cells-derived endothelial and mural cells. PLoS One. Feb. 27, 2008;3(2):e1666. 11 pages.
Yamamoto et al., Circulating adiponectin levels and risk of type 2 diabetes in the Japanese. Nutr Diabetes. Aug. 18, 2014;4:e130. 5 pages.
Yamashita et al., Flk1-positive cells derived from embryonic stem cells serve as vascular progenitors. Nature. Nov. 2, 2000;408(6808):92-6.
Yang et al., Human cardiovascular progenitor cells develop from a KDR+ embryonic-stem-cell-derived population. Nature. May 22, 2008;453(7194):524-8.
Yingling et al., Development of TGF-beta signalling inhibitors for cancer therapy. Nat Rev Drug Discov. Dec. 2004;3(12):1011-22.
Yoder, Human endothelial progenitor cells. Cold Spring Harb Perspect Med. Jul. 2012;2(7):a006692, 14 pages.
Yuan et al., Cell-surface marker signatures for the isolation of neural stem cells, glia and neurons derived from human pluripotent stem cells. PLoS One. Mar. 2, 2011;6(3):e17540. 16 pages.
Zernecke et al., Delivery of microRNA-126 by apoptotic bodies induces CXCL12-dependent vascular protection. Sci Signal. Dec. 8, 2009;2(100):ra81.

(56) References Cited

OTHER PUBLICATIONS

Zhang et al., Microvesicles derived from human umbilical cord mesenchymal stem cells stimulated by hypoxia promote angiogenesis both in vitro and in vivo. Stem Cells Dev. Dec. 10, 2012;21(18):3289-97.

Zhao et al., Isolation and initial application of a novel peptide that specifically recognizes the neural stem cells derived from rhesus monkey embryonic stem cells. J Biomol Screen. Jul. 2010;15(6):687-94.

Zhao et al., Novel peptide ligands that bind specifically to mouse embryonic stem cells. Peptides. Nov. 2010;31(11):2027-34.

Zhong et al., Association of serum omentin-1 levels with coronary artery disease. Acta Pharmacol Sin. Jul. 2011;32(7):873-8.

Zilberfarb et al., Human immortalized brown adipocytes express functional beta3-adrenoceptor coupled to lipolysis. J Cell Sci. Apr. 1997;110 ( Pt 7):801-7.

Zou et al., Two functional microRNA-126s repress a novel target gene p21-activated kinase 1 to regulate vascular integrity in zebrafish. Circ Res. Jan. 21, 2011;108(2):201-9.

Zwaka et al., A germ cell origin of embryonic stem cells? Development. Jan. 2005;132(2):227-33.

Kawasaki et ai., Vascular Repair by Tissue-Resident Endothelial Progenitor Cells in Endotoxin-Induced Lung Injury. Am J Respir Cell Mol Biol. Oct. 2015;53(4):500-12.

Ramskold et al., An abundance of ubiquitously expressed genes revealed by tissue transcriptome sequence data. PLoS Comput Biol. 2009;5(12):e1000598, 11 pages.

\* cited by examiner

B. hESC-derived PC/PSCs are highly scalable

A. hESC-derived PC/PSC morphology

FIG. 8

| Cells | Source | Mesenchymal Potency | | Perivascular Function | |
|---|---|---|---|---|---|
| | | Adipo | Osteo | Tube Forming | Tube Stabilizing |
| 017-PC-A | hESC | - | - | - | - |
| 017-PC-M | hESC | - | - | + | + |
| 017-PC-O | hESC | - | + | - | - |
| CM02 | hESC | - | + | +/- | - |
| E164 | hESC | - | + | +/- | - |
| BM-MSC | Bone | + | + | +/- | + |
| Pl-PC | Placenta | - | + | - | - |

PERIVASCULAR STROMAL CELLS FROM PRIMATE PLURIPOTENT STEM CELLS

CROSS-REFERENCE TO RELATED APPLICATIONS

This application claims priority to U.S. Provisional Application No. 61/941,439, filed on Feb. 18, 2014 and U.S. Provisional Application No. 62/014,639, filed on Jun. 19, 2014, the entire contents of both of which are hereby incorporated in their entirety.

FIELD OF THE INVENTION

This invention relates to the field of stem cell biology. More specifically, this invention relates to in-vitro differentiation of primate pluripotent stem (pPS) cells into perivascular stromal cells/pericyte-like cells and methods of using the same.

BACKGROUND

Pericytes, also known as Rouget cells or mural cells, are endothelium-associated cells present in small blood vessels. Pericytes play an important role in normal vascular structure and function, including maintenance of the blood-brain barrier, tissue repair and regeneration [1, 2, 6, 20-22]. As integral part of vasculature, equivalent to smooth muscle cells for large blood vessels, pericytes wrap around endothelial cells of capillaries, small arterioles and venules, providing a physical barrier and regulating blood flow to the tissue. Pericytes are embedded in basement membrane where they communicate with endothelial cells by means of both direct physical contact and paracrine signaling [1]. Pericytes are also a key component of the neurovascular unit, which includes endothelial cells, astrocytes, and neurons [2]. Additionally, pericytes function in the clearance and phagocytosis of cellular debris and in tissue repair and regeneration [1]. Improper functioning of pericytes can result in abnormal vasculature and contribute to a variety of pathological conditions including ischemic conditions, neurodegenerative disorders, diabetic retinopathy and hepatic fibrosis [1, 3-6, 22].

Pericytes share many properties with mesenchymal stromal cells (MSCs) and can be thought of as perivascular stromal cells (PSCs) that are present throughout the body and serve as a source of repair cells that become activated during injury [7]. Previous studies have identified human pluripotent cell derived pericyte-like cells with both angiogenic and MSC-like multilineage potential [8,9]. However, recent mouse studies suggest that specialized subtypes of perivascular cells may exist with much more restricted lineage potential [10-11].

Replacement of pericytes using cell therapy may be useful for treating a number of vascular diseases. Primary pericytes as a source of cells for cell therapy are limited in supply, heterogeneous and have limited scalability. The use of autologous cells for therapy could be limited by the age or health status of the patient. Derivation of pericytes/perivascular stromal cells (PC/PSC) from human embryonic or induced pluripotent stem cells, therefore offers the possibility of a renewable and scalable source of uniform cells for research and development of regenerative therapies.

There is a need for improved methods for developing a renewable, scalable source of pericytes/perivascular stromal cells for cell therapy and research. Moreover, there is a need for improved pericyte-like cells for use in vascular research and in angiogenic treatment of various vascular conditions. The invention described herein meets these needs as well as other needs in the field.

SUMMARY OF THE INVENTION

In various embodiments described herein, the invention provides, inter alia, methods of generating pericyte-like cells, including pericyte progenitor cells, perivascular stromal cells (PSC), cells with characteristics of immature pericytes, cells with characteristics of mature pericytes, pericyte-like cells with osteogenic potential and pericyte-like cells with angiogenic potential, from primate pluripotent stem (pPS) cells.

In certain embodiments, the invention provides a method for differentiating pluripotent stem cells into pericyte-like cells, comprising: 1) obtaining embryoid bodies from pluripotent stem cells; 2) seeding embryoid bodies at an appropriate concentration in low attachment plates; 3) culturing the embryoid bodies in suspension in the presence of appropriate factors; and 4) dissociating the embryoid bodies and transferring the dissociated cells to adherent plates for further culturing in the presence of appropriate factors. In some embodiments, the embryoid bodies are formed under high cell density conditions. In certain embodiments, the seeding density for step 1 is equal to or higher than $1.5 \times 10^6$ cells/mL. In other embodiments, the seeding density for step 1 is equal to or higher than $3 \times 10^6$ cells/mL. In certain embodiments, the culturing is performed in a medium comprising a BMP. In certain embodiments, the BMP is BMP4. In yet other embodiments, further culturing of step 4 is performed in a medium comprising basic fibroblast growth factor, optionally also comprising a TGFβ signaling inhibitor. In other embodiments, the method comprises an additional step of dissociating and harvesting cells of step 4, and expanding said cells by further culturing on adherent plates in the presence of appropriate factors.

In another embodiment, the invention provides a method for differentiating pluripotent stem cells into pericyte-like cells, the method comprising: 1) obtaining embryoid bodies from pluripotent stem cells under high cell density conditions; 2) seeding embryoid bodies in low attachment plates; 3) culturing the embryoid bodies in suspension in the presence of BMP4, Activin A and bFGF; 4) dissociating the embryoid bodies and transferring the dissociated cells to adherent plates for further culturing in the presence of BMP4, bFGF, VEGF-A and a p160ROCK inhibitor; and 5) dissociating and harvesting cells of step 4, and expanding said cells by further culturing on adherent plates in the presence of BMP4, bFGF, and a TGFβ signaling inhibitor.

In certain embodiments, the invention provides a method for generating pericyte-like cells, the method comprising: 1) culturing the embryoid bodies in suspension in the presence of appropriate factors; and 2) dissociating the embryoid bodies and transferring the dissociated cells to adherent plates for further culturing in the presence of appropriate factors. In certain embodiments, the culturing is performed in a medium comprising a BMP. In certain embodiments, the BMP is BMP4. In yet other embodiments, further culturing of step 2 is performed in a medium comprising basic fibroblast growth factor, optionally also comprising a p160ROCK inhibitor. In other embodiments, the method comprises an additional step of dissociating and harvesting cells of step 3, and expanding said cells by further culturing on adherent plates in the presence of appropriate factors.

In other embodiments, the invention provides a CD146 expressing cell that is the in vitro differentiated progeny of a human pluripotent stem cell. In some embodiments, the cell further expresses CD73 and/or CD105. In other embodiments, the cell further expresses PDGFRβ and/or NG2. In certain embodiments, the cell possesses the morphological and/or functional characteristics of an immature pericyte. In other embodiments, the cell possesses the morphological and/or functional characteristics of a mature pericyte. In certain embodiments, the cell is a mesenchymal progenitor cell. In other embodiments, the cell is capable of further differentiation into an osteoblast. In yet other embodiments, the cell is capable of forming tube-like vascular structures alone or in co-culture with endothelial cells.

In other embodiments, the invention provides a pericyte-like cell with CD146+/CD73+/CD31−/CD34− expression profile that is the in vitro differentiated progeny of a human pluripotent stem cell. In some embodiments, the cell does not express CDC133 and PDPN. In certain embodiments, the cell expresses one or more markers chosen from CD90, CD105, PDGRβ and NG2. In some embodiments, the cell is capable of forming tube-like vascular structures alone or in co-culture with endothelial cells.

In other embodiments, the invention provides a pericyte-like cell with CD146+/CD73+/CD31−/CD34+/− expression profile that is the in vitro differentiated progeny of a human pluripotent stem cell. In certain embodiments, the cell expresses one or more markers chosen from CD90 and CD105. In some embodiments, the cell is capable of differentiating into an osteoblast. In some embodiments, the cell further expresses PDPN, optionally also expressing CD133. In some embodiments, the cell is capable of further differentiation into a more mature cell type of mesenchymal cell lineage.

In some embodiments, the invention provides a method of forming a tube-like vascular structure, comprising contacting an endothelial cell with a pericyte-like cell that is the in vitro differentiated progeny of a human pluripotent stem cell and that is further capable of forming tubular structures alone or in co-culture with endothelial cells.

In other embodiments, the invention provides a population of pericyte-like cells wherein at least 70% of cells express CD146. In other embodiments, at least 80% of cells express CD146. In other embodiments, at least 90% of cells express CD146. In some embodiments, the population of cells additionally express CD73 and/or CD105.

In another embodiment, the invention provides a method for treating a subject in need of therapy, comprising administering to the subject pericyte-like cells that are the in vitro differentiated progeny of a human pluripotent stem cell. In some embodiments, the subject in need of therapy needs vascular tissue regeneration or repair. In some embodiments, the subject in need of therapy is human. In some embodiments, the pericyte-like cells are administered in a biologically acceptable carrier or delivery system. In some embodiments, the delivery system comprises a hydrogel.

In another embodiment, the invention provides a pharmaceutical composition comprising isolated pericyte-like cells that are the in vitro differentiated progeny of human pluripotent stem cells and a biologically acceptable carrier or delivery system.

In another embodiment, the invention provides a system or kit for generating pericyte-like cells, comprising a culture medium and appropriate factors for differentiating pluripotent stem cells into pericyte like cells.

In yet another embodiment, the invention provides a kit comprising pericyte-like cells/perivascular stromal cells that are the in vitro differentiated progeny of human pluripotent stem cells, wherein the pericyte-like cells/perivascular cells are capable of forming vascular structures alone or in co-culture with endothelial cells. In some embodiments, the kit further comprises endothelial cells. In other embodiments, the kit further comprises culture media and/or appropriate factors to be added to the media. In yet other embodiments, the kit further comprises anti- or pro-angiogenic factors. In yet other embodiments, the kit further comprises a substrate or an extracellular matrix component for culturing cells.

DESCRIPTION OF DRAWINGS

For a fuller understanding of the nature and advantages of the present invention, reference should be had to the following detailed description taken in connection with the accompanying drawings, in which:

FIG. 8 shows a summary of the functional analysis data of the pericyte-like cells/perivascular stromal cells of the invention.

DETAILED DESCRIPTION

Figure 1:
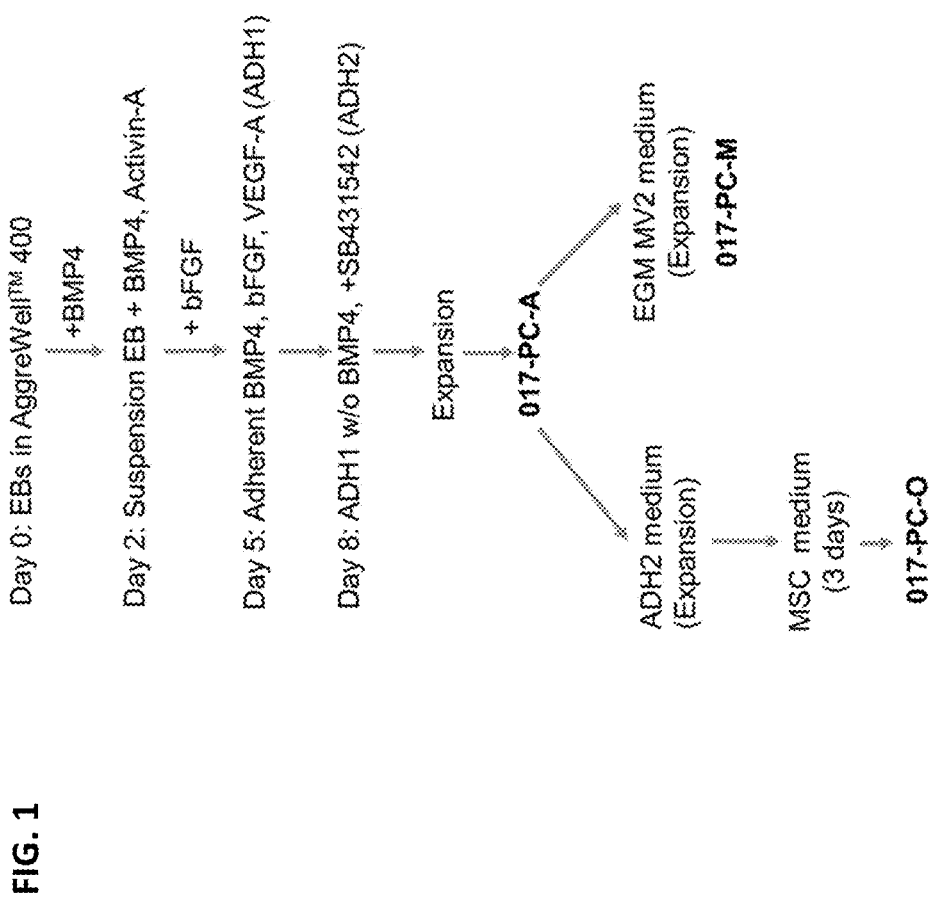
FIG. 1 is a schematic diagram of the pericyte derivation protocol described in Example 1.

Before the present compositions and methods are described, it is to be understood that this invention is not limited to the particular processes, compositions, or methodologies described, as these may vary. It is also to be understood that the terminology used in the description is for the purpose of describing the particular versions or embodiments only, and is not intended to limit the scope of the present invention which will be limited only by the appended claims. Unless defined otherwise, all technical and scientific terms used herein have the same meanings as commonly understood by one of ordinary skill in the art. Any methods and materials similar or equivalent to those described herein can be used in the practice or testing of embodiments of the present disclosure.

The present invention relates, at least in part, to the discovery that specialized subtypes of pericytes/perivascular cells with distinct functions and more restricted lineage potential exist and can be derived from pPS cells. Previous attempts to derive pericytes from pluripotent stem cells have yielded cells that have both angiogenic and MSC-like multilineage potential [8, 9].

The present invention provides a directed differentiation protocol for obtaining high yields of a scalable population of pericyte progenitor cells that are capable of further directed differentiation towards two distinct functional subtypes. One population of cells is osteogenic and lacks both adipogenic and angiogenic potential, whereas the other population of cells is angiogenic and lacks osteogenic and adipogenic potential. The cells of the present invention are scalable, homogenous and may potentially be used in research and cell therapy.

Definitions

The term "embryoid bodies" (EBs), as used herein, refers to heterogeneous clusters comprising undifferentiated, partially differentiated and fully differentiated cells that appear when primate pluripotent stem cells are allowed to differentiate in a non-specific fashion (e.g., by culturing pPS cells in suspension cultures or aggregates).

As used herein, "embryonic stem cell" (ES) refers to a pluripotent stem cell that is 1) derived from a blastocyst before substantial differentiation of the cells into the three germ layers; or 2) alternatively obtained from an established cell line. Except when explicitly required otherwise, the term includes primary tissue and established cell lines that bear phenotypic characteristics of ES cells, and progeny of such lines that have the pluripotent phenotype. The ES cell may be human ES cells (hES). Prototype hES cells are described by Thomson et al. (Science 282:1145 (1998); and U.S. Pat. No. 6,200,806), and may be obtained from any one of number of established stem cell banks such as UK Stem Cell Bank (Hertfordshire, England) and the National Stem Cell Bank (Madison, Wis., United States).

As used herein, "primate pluripotent stem cells" (pPS) refers to cells that may be derived from any source and that are capable, under appropriate conditions, of producing primate progeny of different cell types that are derivatives of all of the 3 germinal layers (endoderm, mesoderm, and ectoderm). pPS cells may have the ability to form a teratoma in 8-12 week old SCID mice and/or the ability to form identifiable cells of all three germ layers in tissue culture. Included in the definition of primate pluripotent stem cells are embryonic cells of various types including human embryonic stem (hES) cells, (see, e.g., Thomson et al. (1998) Science 282:1145) and human embryonic germ (hEG) cells (see, e.g., Shamblott et al., (1998) Proc. Natl. Acad. Sci. USA 95:13726,); embryonic stem cells from other primates, such as Rhesus stem cells (see, e.g., Thomson et al., (1995) Proc. Natl. Acad. Sci. USA 92:7844), marmoset stem cells (see, e.g., (1996) Thomson et al., Biol. Reprod. 55:254,), stem cells created by nuclear transfer technology (U.S. Patent Application Publication No. 2002/0046410), as well as induced pluripotent stem cells (see, e.g., Yu et al., (2007) Science 318:5858); Takahashi et al., (2007) Cell 131(5):861). The pPS cells may be established as cell lines, thus providing a continual source of pPS cells.

As used herein, "induced pluripotent stem cells" (iPS) refers to embryonic-like stem cells obtained by de-differentiation of adult somatic cells. iPS cells are pluripotent (i.e., capable of differentiating into at least one cell type found in each of the three embryonic germ layers). Such cells can be obtained from a differentiated tissue (e.g., a somatic tissue such as skin) and undergo de-differentiation by genetic manipulation which re-programs the cell to acquire embryonic stem cell characteristics. Induced pluripotent stem cells can be obtained by inducing the expression of Oct-4, Sox2, Kfl4 and c-Myc in a somatic stem cell. Thus, iPS cells can be generated by retroviral transduction of somatic cells such as fibroblasts, hepatocytes, gastric epithelial cells with transcription factors such as Oct-3/4, Sox2, c-Myc, and KLF4 [Yamanaka S, Cell Stem Cell. 2007, 1(1):39-49; Aoi T, et al., Generation of Pluripotent Stem Cells from Adult Mouse Liver and Stomach Cells. Science. 2008 Feb. 14. (Epub ahead of print); 111 Park, Zhao R, West J A, et al. Reprogramming of human somatic cells to pluripotency with defined factors. Nature 2008; 451:141-146; K Takahashi, Tanabe K, Ohnuki M, et al. Induction of pluripotent stem cells from adult human fibroblasts by defined factors. Cell 2007; 131:861-872]. Other embryonic-like stem cells can be generated by nuclear transfer to oocytes, fusion with embryonic stem cells or nuclear transfer into zygotes if the recipient cells are arrested in mitosis.

It will be appreciated that embryonic stem cells (such as hES cells), embryonic-like stem cells (such as iPS cells) and pPS cells as defined infra may all be used according to the methods of the present invention.

The term "subject," as used herein, includes, but is not limited to, humans, non-human primates and non-human vertebrates such as wild, domestic and farm animals including any mammal, such as cats, dogs, cows, sheep, pigs, horses, rabbits, rodents such as mice and rats. In some embodiments, the term "subject," refers to a male. In some embodiments, the term "subject," refers to a female.

The terms "treatment," "treat" "treated," or "treating," as used herein, can refer to both therapeutic treatment or prophylactic or preventative measures, wherein the object is to prevent or slow down (lessen) an undesired physiological condition, symptom, disorder or disease, or to obtain beneficial or desired clinical results. In some embodiments, the term may refer to both treating and preventing. For the purposes of this disclosure, beneficial or desired clinical results may include, but are not limited to one or more of the following: alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response. Treatment also includes prolonging survival as compared to expected survival if not receiving treatment.

The terms "pericyte" and "pericyte-like" as used herein, refer to mature pericytes, immature pericytes, pericyte progenitor cells, perivascular stromal cells (PSC), placental pericytes, brain vessel pericytes, pericytes of other tissue origin and other cells possessing functional and morphological characteristics of pericytes. The terms "pericyte", "pericyte-like", and "perivascular stromal cells" (PSC) are used interchangeably herein and should be understood to be referring to the same type of cells.

"CD146", as used herein, refers to a cell surface protein encoded by the MCAM gene in humans. CD146, also known as the melanoma cell adhesion molecule (MCAM) or cell surface glycoprotein MUC18, is a 113 kDa cell adhesion molecule, commonly used as a marker for endothelial cell lineage.

"CD73", also known as 5'-nucleotidase (5'-NT), also known as ecto-5'-nucleotidase, is an enzyme that in humans is encoded by the NT5E gene. CD73 is commonly used as a marker for multipotent mesenchymal stromal cells (MSCs).

"CD105", also known as endoglin, END, FLJ41744, HHT1, ORW and ORW1, is a type I membrane glycoprotein located on cell surfaces and is part of the TGF beta receptor complex. It has a crucial role in angiogenesis and is commonly used as a marker for MSCs. CD105 is encoded by the ENG gene in humans.

"CD90", also known as Thy-1, is a 25-37 kDa conserved cell surface protein that is N-glycosylated, glycophosphatidylinositol (GPI)-anchored and has a V-like immunoglobulin domain. CD90 was originally discovered as a thymocyte antigen and is encoded by the THY1 gene. It is commonly used as a marker for a variety of stem cells, including MSCs.

"CD34" is a cell surface glycoprotein that functions as a cell-cell adhesion factor. The CD34 protein is a member of a family of single-pass transmembrane sialomucin proteins that are expressed on early hematopoietic and vascular-associated tissue. CD34 is encoded in humans by the CD34 gene. It is commonly used as a marker for hematopoietic and/or vascular endothelial cells.

"CD31", also known as PECAM-1 (platelet endothelial cell adhesion molecule) is a protein in the immunoglobulin superfamily found on the surface of platelets, monocytes, neutrophils, and some types of T-cells. CD31 makes up a large portion of endothelial cell intercellular junctions. CD31 is encoded in humans by the PECAM-1 gene and is commonly used as a marker for endothelial cells.

"CD133" (cluster of differentiation 133), also known as prominin 1, PROM1, AC133, CORD12, MCDR2, RP41, and STGD4, is a glycoprotein whose function is presently unknown. CD133 is a member of 5-transmembrane glycoproteins that specifically localize to cellular protrusions. CD133 is expressed in hematopoietic stem cells, endothelial progenitor cells, neuronal and glial stem cells, gliobastomas and various brain tumors, and is commonly used as a marker for stem cells, including cancer stem cells. CD133 is encoded in humans by the PROM1 gene.

"NG2" (neuron glial antigen 2), also known as chondroitin sulfate proteoglycan 4 (CSPG4) or melanoma-associated chondroitin sulfate proteoglycan (MCSP), is a chondroitin sulfate proteoglycan. NG2 is a cell surface component that is expressed in both angiogenic and angiogenic neovasculature. It is commonly used as a marker for smooth muscle cells and vascular pericytes. NG2 is encoded in humans by the CSPG4 gene.

"PDGFRβ" (platelet derived growth factor receptor beta), also known as CD140B, IBGC4, JTK12, PDGFR-1 or PDGFR1, is a receptor tyrosine kinase (RTK) for members of the platelet-derived growth factor family. The functional PDGFR is a dimer composed of two polypeptides, either two PDGFRβ peptides (beta homodimer), a PDGFRβ/PDGFRα heterodimer or two PDGFRα peptides (alpha homodimer); the dimer formation is dictated by the identity of growth factor bound to a receptor monomer. PDGFRβ is commonly used as marker for mesenchymal cells and perivascular cells, although expression of PDGFRβ is highly varied among vessel types in tissues and organs [12]. PDGFRβ is encoded in humans by the PDGFRβ gene.

"Podoplanin" (PDPN), also known as AGGRUS, GP36, GP40, Gp38, HT1A-1, OTS8, T1A, and T1A-2, is a type-I, integral membrane, O-glycosylated glycoprotein with diverse distribution in human tissues. The specific function of PDPN has not been determined. Recent studies indicate that in lymphatic endothelial cells, podoplanin plays a role in proper formation of linkages between the cardiovascular system and the lymphatic system [13]. Podoplanin is expressed in lymphatic progenitor cells and later during development in lymphatic endothelial cells; it is used as a specific marker for lymph vessel endothelial cells. Podoplanin is encoded in humans by the PDPN gene.

Cells of the Invention

In certain embodiments the present invention provides methods for generating pericyte-like cells. Pericyte-like cells that may be used in any of the embodiments of the invention include, but are not limited to, mature pericytes, immature pericytes, pericyte progenitor cells, perivascular stromal cells and cells expressing certain markers, including but not limited to, CD146, CD73, CD105, PDGFRβ and NG2. In certain embodiments, the pericyte-like cells of the invention express CD90, CD133 and/or PDPN.

The appearance and morphological characteristics of pericytes may vary according to the tissue source from which the cells are derived [6]. Pericyte morphology may range from that of the typical CNS pericyte, a flattened, or elongated, stellate-shaped solitary cell with multiple cytoplasmic processes encircling the capillary endothelium and contacting a large abluminal vessel area, to that of a mesangial cell of the kidney glomerulus, rounded, compact and contacting a minimal abluminal vessel area, making only focal attachments to the basement membrane [6].

Phenotype/marker expression is also used in identifying and characterizing pericytes. Included in the markers commonly found on pericytes and pericyte-like cells are CD146, CD105, PDGFRβ and NG2. According to the embodiments of the present invention, PDPN and CD133 are markers for immature pericytes or pericyte progenitor cells.

In some embodiments, the present invention provides methods for generating immature pericytes or pericyte progenitor cells. Immature pericytes/pericyte progenitor cells are more primitive cells in the hierarchy of pericyte differentiation and are capable of further differentiating into other cell types of mesenchymal lineage. Immature pericytes/pericyte progenitor cells may be multipotent or oligopotent. In some embodiments, immature pericytes/pericyte progenitor cells of the present invention are capable of differentiating into cells with osteogenic potential. In other embodiments, immature pericytes/pericyte progenitor cells of the present invention are capable of differentiating into osteoblasts. In other embodiments, immature pericytes/pericyte progenitor cells of the present invention are capable of differentiating into cells with angiogenic potential.

Immature pericytes or pericyte progenitor cells may also be characterized according to their marker expression profile. In some embodiments, immature pericytes/pericyte progenitor cells of the present invention express stemness marker CD133. In other embodiments, immature pericytes/pericyte progenitor cells of the present invention express podoplanin (PDPN). In yet other embodiments, immature pericytes/pericyte progenitor cells of the present invention express CD133 and PDPN. In some embodiments, the immature pericytes/pericyte progenitor cells of the present invention have CD146+/CD34−/CD31− marker expression signature. In other embodiments, the immature pericytes/pericyte progenitor cells of the present invention have CD146+/CD34+/CD31− marker signature. In yet other embodiments, the immature pericytes/pericyte progenitor cells of the present invention express CD73. In yet other embodiments, the immature pericytes/pericyte progenitor cells of the present invention express one or more of the markers CD133, PDPN, CD73, CD146, and CD34. In some embodiments, the immature pericytes/pericyte progenitor cells do not express CD31 and/or CD34.

In some embodiments, the immature pericytes/pericyte progenitor cells of the invention possess osteogenic potential, meaning the cells are able to further differentiate into osteoblasts.

In some embodiments, the present invention provides immature pericytes derived from pPS cells. In some embodiments, the immature pericytes of the present invention express stemness marker CD133. In other embodiments, the-immature pericytes of the present invention express podoplanin (PDPN). In some embodiments, the immature pericytes of the present invention express CD133 and PDPN. In other embodiments, the immature pericytes of the present invention express one or more of the markers CD133, PDPN, CD73, and CD146. In some embodiments, the immature pericytes of the invention do not express CD31 and/or CD34. In other embodiments, the immature pericytes of the invention have CD133+/PDPN+/CD73+/CD146+/CD34−/CD31− marker signature. In other embodiments, the immature pericytes of the present invention have CD133+/PDPN+/CD73+/CD146+/CD34+/CD31− marker signature. In yet other embodiments, the immature pericytes of the present invention have CD133+/PDPN+/CD73+/CD146+/CD34+/CD31+ marker signature.

In some embodiments, the present invention provides methods for generating cells with characteristics of more mature pericytes. Mature pericytes, as defined in the present invention, are further down the pathway of pericyte differentiation and have lost some or all ability to differentiate into other cell types of mesenchymal lineage. Mature pericytes may be distinguished from immature pericytes based on their marker expression profile. Mature pericytes may also be distinguished from immature pericytes and cells of other lineage based on functional assays, such as angiogenic potential in vitro, as measured by the cells' ability to form tube-like microvascular structures.

In some embodiments, the mature pericyte-like cells of the present invention express CD146. In other embodiments, the mature pericyte-like cells of the present invention express CD73 and/or CD105. In some embodiments, the mature pericyte-like cells of the invention express one or more of the markers CD146, CD73, and CD105. In some embodiments, the mature pericyte-like cells of the invention do not express CD31 and/or CD34. In some embodiments, the mature pericyte-like cells of the invention have CD146+/CD73+/CD105+/CD34−/CD31− marker signature. In some embodiments, the mature pericyte-like cells of the invention have CD146+/CD73+/CD105+/CD34−/CD31−/CD133−/PDPN-marker signature. In yet other embodiments, the mature pericyte-like cells of the present invention express PDGFRβ and/or NG2.

In some embodiments, the mature pericyte-like cells of the invention form tube-like vascular structures when co-cultured with endothelial cells. In other embodiments, the mature pericyte-like cells of the invention form tube-like vascular structures alone (in the absence of endothelial cells). The ability to form tubular vascular structures when combined with endothelial cells is commonly used to assess angiogenic potential of putative pericytes or pericyte-like cells.

Methods of Making Pericytes

The present invention provides methods for differentiating primate pluripotent stem (pPS) cells into pericyte-like cells, including pericyte progenitor cells, perivascular stromal cells (PSC), cells with characteristics of immature pericytes, cells with characteristics of mature pericytes, pericyte-like cells with osteogenic potential and pericyte-like cells with angiogenic potential.

In certain embodiments, the derivation process for generating pericytes/perivascular stromal cells follows a protocol used to generate endothelial progenitor cells. By altering the cell density during embryoid body (EB) formation, the resulting cells can be driven either toward endothelial progenitor cells (low cell density during EB formation), or alternatively, toward pericytes/perivascular stromal cells (high cell density during EB formation).

In some embodiments, the invention provides a method of making pericytes/perivascular stromal cells, comprising: 1) contacting an EB with BMP; 2) contacting the EB of step 1 with BMP, Activin and FGF; 3) dissociating the EB of step 2 and plating onto an adherent surface; 4) contacting the EB of step 3 with BMP, FGF, Activin and optionally, with p160ROCK inhibitor; and 5) contacting the cells of step 4 with Activin, FGF, VEGF and optionally, with a TGFβ signaling inhibitor.

In certain embodiments, the protocol comprises the following steps. Human embryonic stem cells are seeded for embryoid body formation under high cell density conditions. At about 24 hours, BMP4 is added to the medium. At about 48 hours, formed embryoid bodies (EBs) are collected, pooled together and transferred to low adhesion plates where they are cultured in a medium comprising BMP4, Activin A and bFGF. The cells are cultured in suspension for three days, at which point (day 5), the EBs are collected, dissociated and plated onto adherent plates in a medium comprising BMP4, bFGF, Activin A and VEGF-A, optionally also comprising a p160ROCK inhibitor. The cells are cultured for another three days, at which point (day 8), the adherent cells are harvested and are expanded by passaging the cells onto adherent plates in a medium comprising bFGF, Activin A, and VEGF-A, optionally also comprising a TGFβ signaling inhibitor. The cells are cultured for an additional three days at which point the candidate pericytes/pericyte progenitor cells are harvested and banked. The banked cells are expanded to yield common pericyte progenitor cells, which can undergo further directed differentiation to yield two distinct types of pericyte-like cells: 1) pericyte-like cells with osteogenic potential, but no angiogenic potential and 2) pericyte-like cells with angiogenic, but no osteogenic potential.

In certain embodiments, the differentiation is performed as in Example 1. In certain other embodiments, the protocol is as described in Example 1 except that pericyte-like cells with angiogenic or osteogenic potential (017-PC-M and 017-PC-O cells, respectively) are generated by passaging the common progenitor 017-PC-A cells for 3-4 passages in ADH2 after day 8 of the differentiation protocol and then switching the media to either mesenchymal stromal cell medium (osteogenic pericyte-like cells) or endothelial cell medium (angiogenic pericyte-like cells).

In certain embodiments, at least one BMP is included in the culture medium between days 1-8, or between days 2-8, or between days 3-5. In some embodiments, the BMP is BMP4. In certain embodiments, a first concentration of one or more BMPs is included in the culture medium for a first period of time and a second concentration of one or more BMPs is included in the culture medium for second period of time.

In certain embodiments, at least one BMP is included in the culture medium at a concentration between 1 ng/mL and 200 ng/mL, or between 5 ng/mL and 100 ng/mL, or between 10 ng/mL and 50 ng/mL. As a nonlimiting example, 20 ng/mL total concentration of one or more BMPs may be present in the culture medium between days 1 and 5, and 10 ng/mL total concentration of one or more BMPs may be present in the culture medium between days 5 and 8.

In certain embodiments, at least one Activin is included in the culture medium between days 0 and 5, or between days 2 and 4. In some embodiments, the Activin is Activin A.

In certain embodiments, at least one fibroblast growth factor (FGF) is included in the culture medium between days 3-11, or between days 5-8. In some embodiments, the FGF is bFGF, also known as FGF2. In certain embodiments, a first concentration of one or more FGFs is included in the culture medium for a first period of time and a second concentration of one or more FGFs is included in the culture medium for second period of time.

In certain embodiments, at least one FGF is included in the culture medium at a concentration between 1 ng/mL and 100 ng/mL, or between 2 ng/mL and 25 ng/mL, or between 5 ng/mL and 10 ng/mL. As a nonlimiting example, 8 ng/mL total concentration of one or more FGFs may be present in the culture medium between days 3 and 11.

Additional components to the medium may include other growth factors and specific inhibitors or activators of signaling molecules. In a nonlimiting example, adherent cells are cultured during days 5-8 in the presence of a specific biochemical inhibitor of rho-associated protein kinase p160ROCK. In another nonlimiting example, adherent cells are cultured during days 8-11 in the presence of a specific biochemical inhibitor of TGFβ signaling.

In certain embodiments, the culture medium used during the differentiation steps is a defined (serum-free) medium. In other embodiments, the culture medium used during the differentiation steps contains less than 0.25% serum, or less than 0.5% serum, or less than 1.0% serum, or less than 5% serum, or less than 10% serum.

In certain embodiments, the differentiating cells are cultured on a substrate. Substrates include, but are not limited to, collagen, laminin, fibronectin, vitronectin, hylauronate poly-L-Lysine-coated tissue culture plastic, and MATRIGEL®.

Certain solid surfaces may be used in the culturing of cells. Those solid surfaces include, but are not limited to, standard cell culturing plates such as 6-well, 24-well, 96-well, or 144-well plates. Certain solid surfaces also include, but are not limited to, microcarriers and disks. In certain embodiments, the microcarriers are beads. Beads come in various forms, including but not limited to, CYTODEX® dextran microcarrier beads with positively charged groups, gelatin/collagen-coated beads, and macroporous microcarrier beads with different porosities. Various beads, including CYTODEX® dextran microcarrier beads, gelatin-coated beads, and macroporous microcarrier beads are commercially available from, e.g., Sigma-Aldrich, St. Louis, Mo. and/or Solohill Engineering Inc., Ann Arbor, Mich. In certain embodiments, the beads are 90-200 μm in size with a total area of 350-500 cm$^2$. In certain embodiments, disks may be used in stirred-tank bioreactors to attach the cells. Disks are commercially available from, e.g., New Brunswick Scientific Co, Inc. (Edison, N.J.). In certain embodiments, the disks are Fibra-cel disks (New Brunswick Scientific Co.), which are polyester/polypropylene disks. A gram of Fibra-cel disks provides a surface area of 1200 cm$^2$.

The solid surface may be made of a variety of substances including, but not limited to, glass or plastic. Plastics include, but are not limited to, polystyrene, polyvinylchloride, polycarbonate, polytetrafluorethylene, melinex, and thermanox. In certain embodiments, the solid surface is three-dimensional in shape. Exemplary three-dimensional solid surfaces are described, e.g., in US 2005/0031598.

Uses of the Cells and the Methods of the Invention

The present invention provides methods to produce large numbers of pericyte-like cells, including pericyte progenitor cells, pericytes at various stages of differentiation, perivascular stromal cells and other cells with morphological, phenotypic and functional characteristics of immature and mature pericytes. Derivation of pericyte-like cells from human embryonic or induced pluripotent stem cells according to the methods of the invention provides a renewable and scalable source of pericytes/perivascular stromal cells for a number of important therapeutic, research, development, and commercial purposes, including vascular tissue regeneration and/or repair and angiogenic treatment of various ischemic conditions.

Screening

The pericyte-like cells of the present invention can be used commercially to screen for factors (such as solvents, small molecule drugs, peptides, oligonucleotides) or environmental conditions (such as culture conditions) that affect the characteristics of such cells and their various progeny. Characteristics may include phenotypic or functional traits of the cells. Other characteristics that may be observed include the differentiation status of the cells; the maturity of the cells and the survival and growth rate of the cells after exposure to the factor.

Thus the pericytes/perivascular stromal cells of the invention may be contacted with one or more factors and the effects of the factors may be compared to an aliquot of the same cells that has not been contacted with the factors.

Other screening applications of this invention relate to the testing of pharmaceutical compounds for their effect on the cells of the invention. Screening may be done either because the compound is designed to have a pharmacological effect on the cells, or because a compound is designed to have effects elsewhere and may have unintended side effects on pericytes/perivascular stromal cells. Other screening applications could include screening compounds for carcinogenic or other toxic effects. The screening can be conducted using any of the pericyte-like cells of the invention in order to determine if the target compound has a beneficial or harmful effect on the target cell.

The reader is referred generally to the standard textbook *In vitro Methods in Pharmaceutical Research*, Academic Press, 1997. Assessment of the activity of candidate pharmaceutical compounds generally involves combining the pericytes/perivascular stromal cells of the invention with the candidate compound, either alone or in combination with other drugs. The investigator determines any change in the morphology, marker phenotype as described infra, or functional activity of the cells, that is attributable to the compound (compared with untreated cells or cells treated with an inert compound), and then correlates the effect of the compound with the observed change.

Cytotoxicity can be determined in the first instance by the effect on cell viability, survival, morphology, and the expression of certain markers and receptors. Effects of a drug on chromosomal DNA can be determined by measuring DNA synthesis or repair. [$^3$H]-thymidine or BrdU incorporation, especially at unscheduled times in the cell cycle, or above the level required for cell replication, is consistent with a drug effect. Unwanted effects can also include unusual rates of sister chromatid exchange, determined by metaphase spread. The reader is referred to A. Vickers (pp. 375-410 in In vitro Methods in Pharmaceutical Research, Academic Press, 1997) for further elaboration.

Where an effect is observed, the concentration of the compound can be titrated to determine the median effective dose (ED50).

Gene Expression

The cells of the invention can be used to prepare a pericyte/perivascular stromal cell cDNA library relatively uncontaminated with cDNA preferentially expressed in cells from other lineages. For example, 017-PC-M, 017-PC-O or 017-PC-M cells are collected by centrifugation at 100 g for 10-15 minutes, and then mRNA is prepared from the pellet and reverse transcribed into cDNA using standard techniques (Sambrook et al., supra).

Expression patterns of pericytes/perivascular stromal cells may be compared with other cell types by microarray analysis, for example. Generation of cDNA libraries for microarray analysis would be especially well suited for studying gene expression in pericytes/perivascular stromal cells compared to the undifferentiated pPS cells from which they were derived. Because these cells share essentially identical genomes, comparisons in gene expression (using subtractive hybridization, for example) can be made with little or no background noise. Reducing the number of extraneous phenotypic cells within a cell population will provide improved signal to noise ratios in comparing gene expression in two populations of cells, e.g., the parent pPS cell line giving rise to the progeny pericytes/perivascular stromal cells, and the progeny pericytes/perivascular stromal cells.

The use of microarray in analyzing gene expression is described, for example, by DeRisi et al., Nat Genet 1996 14 (4): 35-46 and Xiang et al., Biotechnol Adv 2000 18(1):35-46. An exemplary method is conducted using a Genetic Microsystems array generator, and an Axon GenePix1M Scanner. Microarrays are prepared by first amplifying cDNA fragments encoding marker sequences to be analyzed, and spotted directly onto glass slides. To compare mRNA preparations from two cells of interest, one preparation is converted into Cy3-labeled cDNA, while the other is converted into Cy5-labeled cDNA. The two cDNA preparations are hybridized simultaneously to the microarray slide, and then washed to eliminate non-specific binding. The slide is then scanned at wavelengths appropriate for each of the labels, the resulting fluorescence is quantified, and the results are formatted to give an indication of the relative abundance of mRNA for each marker on the array.

Alternatively, gene expression analysis may be performed by using next generation sequencing (NGS) methods, generally reviewed in Mardis, Annu Rev Genomics Hum Genet 2008 9:387-402. Use of NGS sequencing platforms, such as those developed by Illumina (Illumina/Solexa Genome Analyzer), Roche (Roche/454/FLX) and Applied Biosystems (Applied Biosystems SOLiD™ System) is contemplated in the present invention.

Animal Testing

The pericyte-like cells of the invention may ultimately be used for maintenance, repair and regeneration of vascular tissue in any subject including human or non-human subjects. To determine the suitability of compositions comprising pericytes/perivascular stromal cells of the invention for therapeutic administration, such compositions can first be tested in a suitable subject such as a rat, mouse, guinea pig, rabbit, cow, horse, sheep, pig, dog, primate or other mammal.

At one level, cells are assessed for their ability to survive and maintain their phenotype in vivo. Cell compositions may be administered to immunodeficient animals (such as SCID mice, or animals rendered immunodeficient chemically or by irradiation). Tissues are harvested after a period of regrowth, and assessed as to whether pluripotent stem derived cells are still present. Functional tests as are known in the art may be performed.

Cell survival may be monitored by administering cells that express a detectable label (such as green fluorescent protein, or β-galactosidase); that have been pre-labeled (for example, with BrdU or [3H]-thymidine), or by subsequent detection of a constitutive cell marker (for example, by using a species-specific antibody). The presence and phenotype of the administered cells can be assessed by immunohistochemistry or ELISA using human-specific antibody, or by RT-PCR analysis using primers and hybridization conditions that cause amplification to be specific for human polynucleotides, according to published sequence data.

In certain embodiments the enriched target cells of the invention may be tested functionally using a known animal model for a particular disease. Several animal models of ischemic heart injury, ischemic stroke, diabetic retinopathy and neurodegenerative disease have been developed and are described and reviewed in literature [15-21, 23]. Any such models may be used to test the functionality of any of the cells of the invention in vivo.

Angiogenesis/Vasculogenesis In Vitro

The cells of the invention may be used for generate vascular tube-like structures in vitro. The tube-like structures may be used to study the biological and physiological properties of small blood vessels.

Therapeutic Use—Vascular Tissue Generation and Osteogenesis/Bone Repair

The isolated pericytes/perivascular stromal cells of the invention may be used for repairing and/or regenerating vascular tissues in a human patient or other subject in need of cell therapy. Alternatively, the cells of the invention may be used for generation of vascular tissue de novo. In other embodiments, cells of the invention may be used for osteogenesis and/or bone repair in a subject in need of cellular therapy.

Cells of the invention possessing ability to form vascular tubes and constructs (such as the 017-PC-M cells) may be used for repairing or regenerating vascular tissues. Cells are administered to a subject with a pathological condition requiring vascular tissue repair or regeneration. The following are non-limiting examples of conditions, diseases and pathologies requiring vascular tissue regeneration and/or repair: ischemia, diabetes, diabetic retinopathy, diabetic microangiopathy, small vessel coronary disease, peripheral arterial disease, fibrosis, atherosclerosis and calcific vasculopathy, lymphedema distichiasis, chronic venous insufficiency, pulmonary hypertension, Alzheimer's disease and multiple sclerosis.

Cells of the invention possessing osteogenic potential (such as the 017-PC-O cells) may be used for ability repair or regenerate bone. Cells are administered to a subject with a pathological condition requiring bone repair or regeneration. The following are non-limiting examples of conditions, diseases and pathologies requiring bone repair: osteoporosis, osteopenia, osteochondrosis, osteochondritis, osteogenesis imperfecta, osteomyelitis, osteitis deformans, osteitis fibrosa cystica, impaired bone homeostasis, an accidental/traumatic injury (such as a bone fracture), and a congenital defect that results in absence of bone tissue.

The cells are administered in a manner that permits them to graft or migrate to the intended tissue site and reconstitute or regenerate the functionally deficient area.

Administration of the cells may be achieved by any method known in the art. For example the cells may be administered surgically directly to the organ or tissue in need of a cellular transplant. Alternatively non-invasive procedures may be used to administer the cells to the subject. Examples of non-invasive delivery methods include the use of syringes and/or catheters to deliver the cells into the organ or tissue in need of cellular therapy.

The patient receiving an allograft of enriched target cells of the invention may be treated to reduce immune rejection of the transplanted cells. Methods contemplated include the administration of traditional immunosuppressive drugs like tacrolimus, cyclosporin A (Dunn et al., Drugs 61:1957, 2001), or inducing immunotolerance using a matched population of pluripotent stem derived cells (WO 02/44343; U.S. Pat. No. 6,280,718; WO 03/050251). Alternatively a combination of anti-inflammatory (such as prednisone) and immunosuppressive drugs may be used. The pericyte-like cells of the invention can be supplied in the form of a pharmaceutical composition, comprising an isotonic excipient prepared under sufficiently sterile conditions for human administration. To reduce the risk of cell death upon engraftment, the cells may be treated by heat shock or cultured with 0.5 U/mL erythropoietin 24 hours before administration.

For general principles in medicinal formulation, the reader is referred to Allogeneic Stem Cell Transplantation, Lazarus and Laughlin Eds. Springer Science+Business Media LLC 2010; and Hematopoietic Stem Cell Therapy, E. D. Ball, J. Lister & P. Law, Churchill Livingstone, 2000. Choice of the cellular excipient and any accompanying elements of the composition will be adapted in accordance with the route and device used for administration. The composition may also comprise or be accompanied with one or more other ingredients that facilitate the engraftment or functional mobilization of the enriched target cells. Suitable ingredients may include matrix proteins that support or promote adhesion of the target cell type or that promote vascularization of the implanted tissue.

Antibodies

The cells of the present invention can also be used to prepare antibodies that are specific for markers of pericytes/perivascular stromal cells. Polyclonal antibodies can be prepared by injecting a vertebrate animal with cells of this invention in an immunogenic form. Production of monoclonal antibodies is described in such standard references as Harlow & Lane (1988) Antibodies: A Laboratory Manual, U.S. Pat. Nos. 4,491,632, 4,472,500 and 4,444,887, and Methods in Enzymology 73B:3 (1981).

Systems

The present invention also includes a reagent system, comprising a set or combination of cells that exist at any time during manufacture, distribution, or use. The cell sets comprise any combination of two or more cell populations described in this disclosure, exemplified but not limited to undifferentiated primate pluripotent stem cells and the differentiated progeny of the same. The differentiated progeny may comprise pericyte-like cells, such as pericyte progenitor cells, immature pericytes, mature pericytes, perivascular stromal cells, or the like. The genome of the differentiated progeny and the parental pPS cell line may be at least 95% identical, at least 96% identical, at least 97% identical; at least 98% identical, at least 99% identical, at least 99.5% identical; at least 99.6% identical; at least 99.7% identical; at least 99.8% identical; at least 99.9% identical. Each cell type in the set may be packaged together, or in separate containers in the same facility, or at different locations, at the same or different times, under control of the same entity or different entities sharing a business relationship.

Pharmaceutical Compositions of the Invention

The pericytes/perivascular stromal cells of the invention may be administered to a subject in need of therapy per se. Alternatively, the cells of the invention may be administered to the subject in need of therapy in a pharmaceutical composition mixed with a suitable carrier and/or using a delivery system.

As used herein, the term "pharmaceutical composition" refers to a preparation comprising a therapeutic agent or therapeutic agents in combination with other components, such as physiologically suitable carriers and excipients. The purpose of a pharmaceutical composition is to facilitate administration of a therapeutic agent to a subject.

As used herein, the term "therapeutic agent" refers to the cells of the invention accountable for a biological effect in the subject. Depending on the embodiment of the invention, "therapeutic agent" may refer to isolated pericytes/perivascular stromal cells of the invention, an isolated population of pericytes/perivascular stromal cells of the invention, or an isolated population of cells comprising of pericytes/perivascular cells and endothelial cells. In yet other embodiments, "therapeutic agent" refers to cell culture comprising pericytes/perivascular stromal cells of the invention, alternatively comprising both pericytes/perivascular stromal cells of the invention and endothelial cells.

As used herein, the terms "carrier" "physiologically acceptable carrier" and "biologically acceptable carrier" may be used interchangeably and refer to a diluent or a carrier substance that does not cause significant adverse effects or irritation in the subject and does not abrogate the biological activity or effect of the therapeutic agent. The term "excipient" refers to an inert substance added to a pharmaceutical composition to further facilitate administration of the therapeutic agent.

Modes of administration for a therapeutic agent (either alone or in combination with other biologicals or pharmaceuticals) can be, but are not limited to, sublingual, injectable (including short-acting, depot, implant and pellet forms injected subcutaneously, intramuscularly, or intraperitoneally), or by use of vaginal creams, suppositories, pessaries, vaginal rings, rectal suppositories, intrauterine devices, and transdermal forms such as patches and creams. The therapeutic agent of the invention may be administered as a component of a hydrogel, such as those described in U.S. patent application Ser. No. 14/275,795, filed May 12, 2014, and U.S. Pat. Nos. 8,324,184 and 7,928,069.

Pharmaceutical formulations containing the therapeutic agent of the present disclosure and a suitable carrier can be solid dosage forms which include, but are not limited to, tablets, capsules, cachets, pellets, pills, powders and granules; topical dosage forms which include, but are not limited to, solutions, powders, fluid emulsions, fluid suspensions, semi-solids, ointments, pastes, creams, gels and jellies, and foams; and parenteral dosage forms which include, but are not limited to, solutions, suspensions, emulsions, and dry powder; comprising an effective amount of a polymer or copolymer of the present disclosure. It is also known in the art that the active ingredients can be contained in such formulations with pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and the like. The means and methods for administration are known in the art and an artisan can refer to various pharmacologic references for guidance. For example, Modern Pharmaceutics, Banker & Rhodes, Marcel Dekker, Inc. (1979); and Goodman & Gilman's The Pharmaceutical Basis of Therapeutics, 6th Edition, MacMillan Publishing Co., New York (1980) can be consulted.

The compositions of the present disclosure can be formulated for parenteral administration by injection, e.g., by bolus injection or continuous infusion. The compositions can be administered by continuous infusion subcutaneously over a period of about 15 minutes to about 24 hours. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents.

For oral administration, the compositions can be formulated readily by combining the therapeutic with pharmaceutically acceptable carriers well known in the art. Such carriers enable the therapeutic of the invention to be formulated as tablets, pills, dragees, capsules, liquids, gels, syrups, slurries, suspensions and the like, for oral ingestion by a patient to be treated. Pharmaceutical preparations for oral use can be obtained by adding a solid excipient, optionally grinding the resulting mixture, and processing the mixture of granules, after adding suitable auxiliaries, if desired, to obtain tablets or dragee cores. Suitable excipients include, but are not limited to, fillers such as sugars, including, but not limited to, lactose, sucrose, mannitol, and sorbitol; cellulose preparations such as, but not limited to, maize starch, wheat starch, rice starch, potato starch, gelatin, gum tragacanth, methyl cellulose, hydroxypropylmethyl-cellulose, sodium carboxymethylcellulose, and polyvinylpyrrolidone (PVP). If desired, disintegrating agents can be added, such as, but not limited to, the cross-linked polyvinyl pyrrolidone, agar, or alginic acid or a salt thereof such as sodium alginate.

Dragee cores can be provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active therapeutic doses.

Pharmaceutical preparations which can be used orally include, but are not limited to, push-fit capsules made of gelatin, as well as soft, sealed capsules made of gelatin and a plasticizer, such as glycerol or sorbitol. The push-fit capsules can contain the active ingredients in admixture with filler such as, e.g., lactose, binders such as, e.g., starches, and/or lubricants such as, e.g., talc or magnesium stearate and, optionally, stabilizers. In soft capsules, the active therapeutic can be dissolved or suspended in suitable liquids, such as fatty oils, liquid paraffin, or liquid polyethylene glycols. In addition, stabilizers can be added. All formulations for oral administration should be in dosages suitable for such administration.

For buccal administration, the pharmaceutical compositions can take the form of, e.g., tablets or lozenges formulated in a conventional manner.

For administration by inhalation, the therapeutic for use according to the present disclosure is conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of, e.g., gelatin for use in an inhaler or insufflator can be formulated containing a powder mix of the therapeutic and a suitable powder base such as lactose or starch.

The compositions of the present disclosure can also be formulated in rectal compositions such as suppositories or retention enemas, e.g., containing conventional suppository bases such as cocoa butter or other glycerides.

Pharmaceutical compositions can include suitable solid or gel phase carriers or excipients. Examples of such carriers or excipients include but are not limited to calcium carbonate, calcium phosphate, various sugars, starches, cellulose derivatives, gelatin, and polymers such as, e.g., polyethylene glycols.

The therapeutic agents of the present disclosure can also be administered in combination with other active ingredients, such as, for example, adjuvants, protease inhibitors, or other compatible drugs or compounds where such combination is seen to be desirable or advantageous in achieving the desired effects of the methods described herein.

In some embodiments, the disintegrant component comprises one or more of croscarmellose sodium, carmellose calcium, crospovidone, alginic acid, sodium alginate, potassium alginate, calcium alginate, an ion exchange resin, an effervescent system based on food acids and an alkaline carbonate component, clay, talc, starch, pregelatinized starch, sodium starch glycolate, cellulose floc, carboxymethylcellulose, hydroxypropylcellulose, calcium silicate, a metal carbonate, sodium bicarbonate, calcium citrate, or calcium phosphate.

In some embodiments, the diluent component may include one or more of mannitol, lactose, sucrose, maltodextrin, sorbitol, xylitol, powdered cellulose, microcrystalline cellulose, carboxymethylcellulose, carboxyethylcellulose, methylcellulose, ethylcellulose, hydroxyethylcellulose, methylhydroxyethylcellulose, starch, sodium starch glycolate, pregelatinized starch, a calcium phosphate, a metal carbonate, a metal oxide, or a metal aluminosilicate.

In some embodiments, the optional lubricant component, when present, comprises one or more of stearic acid, metallic stearate, sodium stearylfumarate, fatty acid, fatty alcohol, fatty acid ester, glycerylbehenate, mineral oil, vegetable oil, paraffin, leucine, silica, silicic acid, talc, propylene glycol fatty acid ester, polyethoxylated castor oil, polyethylene glycol, polypropylene glycol, polyalkylene glycol, polyoxyethylene-glycerol fatty ester, polyoxyethylene fatty alcohol ether, polyethoxylated sterol, polyethoxylated castor oil, polyethoxylated vegetable oil, or sodium chloride.

Kits

Also included in the present invention are kits. Such kits can include an agent or composition described herein and, in certain embodiments, instructions for administration. Such kits can be used to obtain the cells of the invention or to facilitate performance of the methods described herein. When supplied as a kit, the different components of the composition can be packaged in separate containers and mixed immediately before use. Components of a kit may include, but are not limited to, pPS cells, culture media and reagents for directed differentiation of the pPS cells into pericytes/perivascular stromal cells.

In some embodiments, the invention provides a kit comprising a pericyte-like cell or perivascular stromal cell as described infra, and at least one container. The kit may optionally include endothelial cells capable of forming vascular tube-like structures.

In other embodiments, the invention provides a kit for studying angiogenesis in vitro. In some embodiments, the kit comprises perivascular stromal cells that are capable of forming vascular tube-like structures alone or in co-culture with endothelial cells. In other embodiments, the kit additionally comprises endothelial cells that when co-cultured with perivascular stromal cells form large angiogenic networks. The kit may optionally include culture media, growth factors, anti- and pro-angiogenic factors, substrate/extracellular matrix for culturing cells and instructions for the angiogenic assay.

EXAMPLES

The following examples are not intended to limit the scope of what the inventors regard as their invention nor are they intended to represent that the experiments below are all or the only experiments performed.

Figure 7:
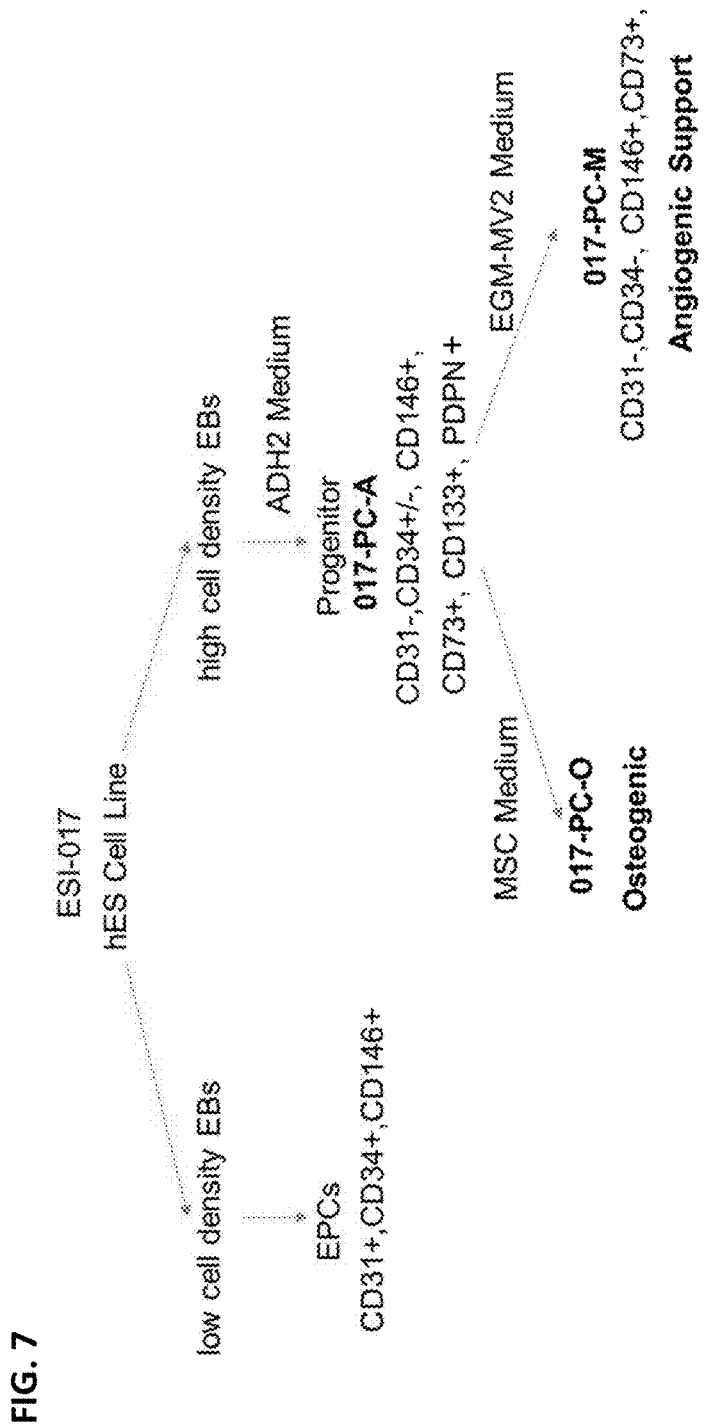
FIG. 7 is a schematic illustrating that endothelial progenitor cells and pericytes/perivascular stromal cells (PC/PSC) of the invention can be derived using the same directed differentiation protocol by altering EB seeding density.

Example 1: Derivation of Pericytes/Perivascular Stromal Cells from Human Embryonic Stem Cells The derivation process for generating pericytes/perivascular stromal cells from human embryonic stem cells was based on a directed differentiation protocol previously used to generate endothelial progenitor cells, described in U.S. patent application Ser. No. 13/477,002. We discovered that by altering the cell density during embryoid body (EB) formation and during the culturing of EBs in suspension, the resulting cells can be driven either toward endothelial progenitor cells (low cell density during EB formation and EB suspension culture), or alternatively, toward pericytes/perivascular stromal cells (high cell density during EB formation and EB suspension culture) (FIG. 7).

The differentiation protocol for obtaining pericytes/perivascular stromal cells (PSC) involved sequential growth factor treatment and is depicted in FIG. 1. The protocol is described in detail below.

NIH-registered human embryonic stem cell line ESI-017 (ESI-BIO) was expanded on growth factor reduced (GFR) MATRIGEL® (Corning Life Sciences) in mTeSR™-1 medium (Stem Cell Technologies). On day 0 (the day of differentiation setup), ESI-017 cells were harvested and dissociated with ACCUTASE® (Life Technologies) to generate single cell suspension. The cells were then seeded in AGGREWELL® 400 (Stem Cell Technologies) plates with microwells (8-well format, with approximately 1200 microwells per each well) at a density of 4000 cells per microwell in STEMLINE® II hematopoietic stem cell expansion medium (Sigma). The plates were centrifuged according to manufacturer's instructions, and then cultured in a 5% $O_2$, 10% $CO_2$, 37° C. incubator. The following day (at about 24 hours), recombinant human BMP4 (human cell-expressed, HumanZyme) was added to 20 ng/mL.

On day 2 (at about 48 hours), the formed Embryoid bodies (EB) from a single AGGREWELL® plate were collected, pooled together and transferred to a 6-well Costar® 3471 (Corning Life Sciences) ultra-low attachment (ULA) plate (1 AGGREWELL® plate to 1 ULA plate), in approximately equal aliquots per well (i.e. plated at a ratio of approximately 8:6) in Stemline II basal medium containing 20 ng/mL BMP4, 10 ng/mL Activin A and 8 ng/mL bFGF (recombinant human basic, Gibco PHG0263), and incubation continued at 5% $O_2$, 10% $CO_2$, 37° C.

On day 5, EBs from a single 6-well ULA plate were collected and dissociated with ACCUTASE®. The cells were then plated onto a single fibronectin-coated T-150 flask and cultured in Stemline® II hematopoietic stem cell expansion medium containing 10 ng/mL BMP4, 8 ng/mL bFGF, 25 ng/mL VEGF-165 and 10 µM p160 ROCK inhibitor Y27632 ("Stage 1 Adhesion Medium", or "ADH1"), and incubation continued at 5% O2, 10% CO2, 37° C.

On day 8, the adherent cells were harvested using ACCUTASE® and cultures were expanded by plating the cells onto 4 uncoated T-225 flasks (1 to 6 ratio) in STEMLINE® II hematopoietic stem cell expansion medium containing 8 ng/mL FGF2, 25 ng/mL VEGF-165, and 10 µM TGFβ signaling inhibitor SB431542 ("Stage 2 Adhesion Medium", or "ADH2"). On day 11, the cells were harvested and banked as candidates for pericytes or pericyte progenitor cells.

Banked candidate cells were later on thawed and expanded in ADH2 medium to yield 017-PC-A cells. 017-PC-A cells were characterized as CD146+/CD31−/CD34− pericyte progenitor cells, in contrast with the CD146+/CD31+/CD34+ endothelial progenitor cells (FIG. 7). 017-PC-A progenitor cells were scalable and capable of further directed differentiation into an osteogenic derivative 017-PC-O and an angiogenic derivative 017-PC-M. The 017-PC-O cells were generated from 017-PC-A cells by switching the cells to MSC medium (DMEM/10% FCS). The 017-PC-M were generated from 017-PC-A cells by switching the cells to endothelial cell growth medium (EGM MV2, PromoCell).

Alternatively, in follow-up-experiments, the 017-PC-M and 017-PC-O cells were generated by passaging cells for 3-4 passages in ADH2 after day 8 of the differentiation protocol and then switching the media to either MSC medium for 017-PC-O cells or EGM MV2 medium for 017-PC-M cells.

The 017-PC-A, 017-PC-O and 017-PC-M cells were maintained and expanded by further culture in their corresponding media. The cultures were fed once every 2-3 days.

Clonal pericytes were derived as previously described [14]. The two lines, E164 and CMO2, were expanded in DMEM with 5% or 10% fetal bovine serum (FBS), respectively.

Figure 2:
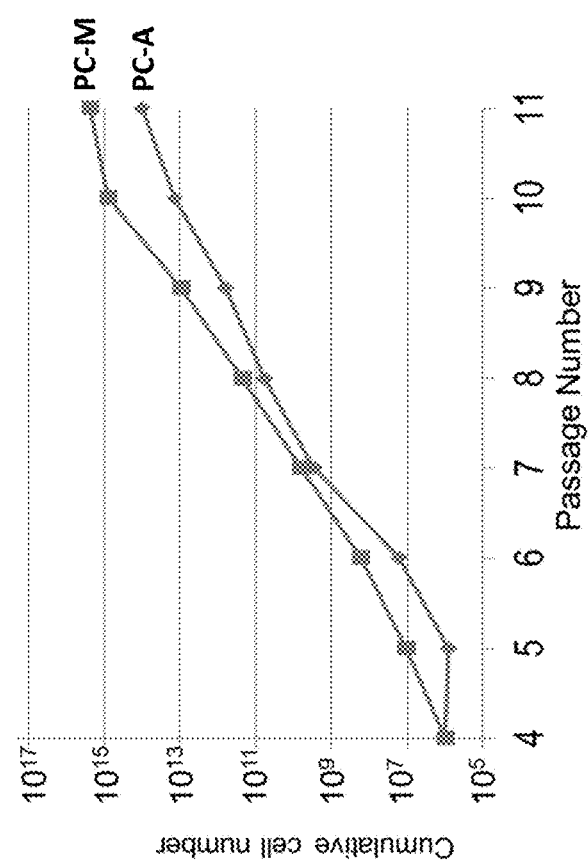
FIG. 2A consists of photo-micrograph images illustrating the morphology of the 017-PC-A and 017-PC-M cells at p12.
FIG. 2B is a graph depicting the growth (cumulative cell number) of 017-PC-A and 017-PC-M cells from p4 to p11.
Figure 2:
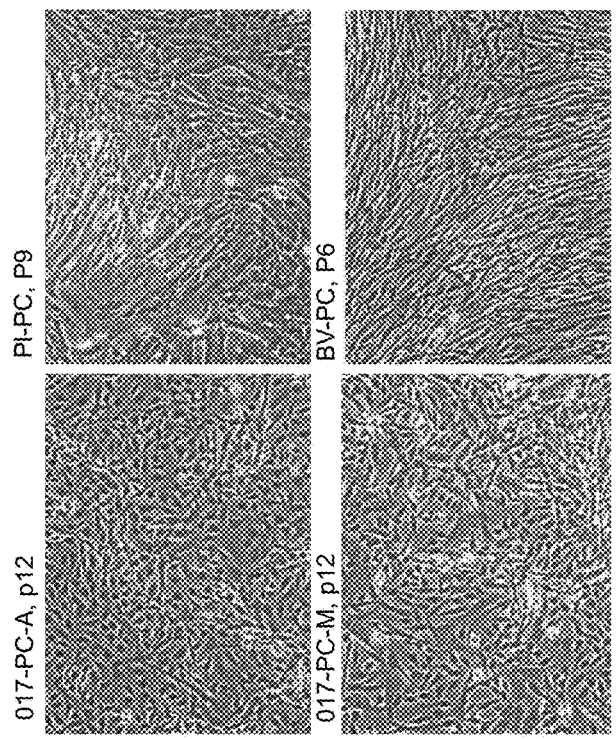

Example 2: Morphological Characteristic and Scalable Growth of Pericyte-Like Cells of the Invention The morphological characteristics of the cultured pericyte-like cells of the invention are illustrated in FIG. 2A. In comparison to primary pericytes (PL-PC and BV-PC, of placental and brain vessel origin, respectively), the 017-PC-A and 017-PC-M appeared as smaller spindle-shaped cells that grew to a high density. After about 18-20 passages, the 017-PC-A and 017-PC-M cells became bigger in size, indicative of hypertrophic senescence, while still exhibiting the same spindle-like shape.

Both 017-PC-A and 017-PC-M expanded well in their corresponding media, and have potential to reach commercial scale, as illustrated in FIG. 2B.

Example 3: Phenotype/Marker Expression Analysis of HESC-Derived Pericyte-Like Cells of the Invention 017-PC-A and 017-PC-M cells as well as clonal lines E164 and CMO2 and control placental (PL-PC) and brain-vessel (BV-PC) primary pericytes were analyzed for expression of a number of surface markers. The markers tested were grouped as following: 1) pericyte: CD146, CD105, PDGFRβ and NG2; 2) mesenchymal: CD73 and CD90; 3) stemness: TRA-1-60, Oct-4, CD133 and podoplanin (PDPN); and 4) hematopoietic/endothelial: CD34, CD31, CD144 and CD45. The antibodies were obtained from commercial vendors as indicated. CD146, CD73, CD90, TRA-1-60, PDPN, CD34, CD31, CD133 and CD45 antibodies were from BioLegend Antibodies; Oct-4 antibody was from Chemicon; CD105 antibody was from BD Biosciences; PDGFRβ and NG2 antibodies were from R&D Systems; CD133 antibody was from Dako.

Marker expression was assessed using flow cytometry (Accurri C6 flow cytometer, BD Bioscience). The data was analyzed with FCS Express 4 (De Novo software).

Figure 3:
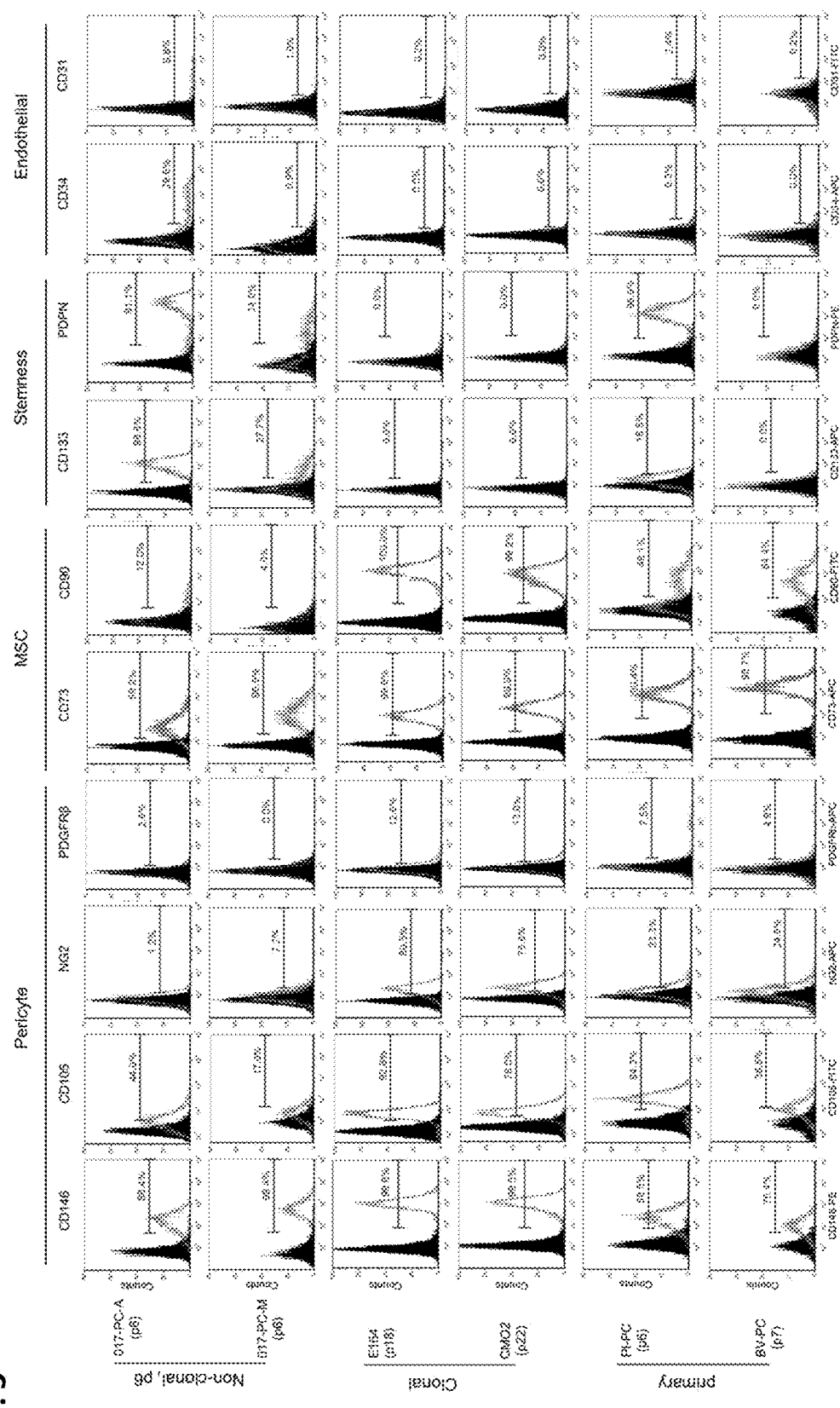
FIG. 3 depicts phenotype/marker expression data from the hES-derived pericyte-like cells of the invention (017-PC-M, 017-PC-A), clonally derived pericyte cell lines E164 and CMO2, and primary pericytes of placental (P1-PC) and brain vessel (BV-PC) origin, as measured by FACS.

The results are depicted in FIG. 3. The hESC-derived 017-PC-A and 017-PC-M pericyte/perivascular stromal cells exhibited an immunophenotype that was similar to primary pericytes (PL-PC and BV-PC), with some noteworthy unique features. All the tested cells (primary pericytes, clonal lines and non-clonal 017-PC-A and 017-PC-M cells) had high level expression CD146 and CD73, with at least 76% and 84% of cells of each population expressing CD146 and CD73 at p6, respectively. High levels of CD146 and CD73 expression persisted throughout early and late passages (FIG. 3 and data not shown). Both the primary pericytes and the two non-clonal cells 017-PC-A and 017-PC-M had a small fraction of cells positive for pericyte markers NG2 (1.2%-24.8%) and PDGFRβ (0-7.5%) at p6, whereas approximately 80% of cells from the clonal lines E164 and CMO2 expressed NG2.

One notable feature shared by the PL-PC primary pericytes and the 017-PC-A cells (and absent in the other tested cells) was high fraction of cells expressing podoplanin (FIG. 3). Podoplanin is expressed in embryonic stem cells and is widely used as marker for lymphatic endothelial cells. The high expression of PDPN in 017-PC-A cells and placental pericytes suggests both cells are relatively immature pericytes (less differentiated and capable of further differentiation into other cell types of mesenchymal lineage), and may have potential to differentiate into supporting cells to lymphatic vessels.

Example 4: Multipotency Assays

017-PC-A, 017-PC-M and 017-PC-O cells as well as clonal lines E164 and CMO2 and control placental (PL-PC) and brain-vessel (BV-PC) primary pericytes were tested for their ability to differentiate into osteoblasts, chondrocytes and adipocytes using standard culture conditions that promote osteogenesis, chondrogenesis and adipogenesis of mesenchymal stem cells (MSCs).

The multipotency assays were performed using Gibco StemPro® Differentiation Kits for Osteogenesis, Chondrogenesis and Adipogenesis, respectively, according to the manufacturer's instructions.

Briefly, for osteogenesis assay, cells were seeded in 24-well plates at $5 \times 10^3$ cells/cm$^2$ in MSC Attachment/Growth Medium (low glucose DMEM, 10% MSC-qualified FBS, 2 mM GLUTAMAX™-I, 5 µg/mL gentamycin). The cells were cultured in MSC Attachment/Growth Medium for 2-3 days, at which point the media was replaced with Complete Osteogenesis Differentiation Medium (STEMPRO® Osteocyte/Chondrocyte Differentiation Basal Medium, STEMPRO® Osteogenesis supplement, 5 µg/mL gentamycin). The cells were further cultured for 21 days, with media replaced every 2-3 days. Alizarin Red staining (for detecting mineral deposits) was performed on day 21 according to manufacturer's instructions, and the stained cells visualized under light microscope.

For chondrogenesis assay, micromass cultures were generated by seeding 5 µL droplets of a cell solution containing $1.6 \times 10^7$ viable cells/mL in MSC Attachment/Growth Medium in the center of 48-well multiwell plates. After the micromass cultures were further cultured for 2 hours under high humidity conditions, Chondrogenesis Differentiation Medium (STEMPRO® Osteocyte/Chondrocyte Differentiation Basal Medium, STEMPRO® Chondrogenesis supplement, 5 µg/mL gentamycin) was added and the cells were further cultured under standard tissue culture conditions (37° C., 5% $CO_2$) for 17 days, with media replaced every 2-3 days. Alcian Blue staining (for detecting sulfated proteoglycans) was performed on day 17 according to the manufacturer's instructions, and the stained cells visualized under light microscope.

For adipogenesis assay, cells were seeded in 24-well plates at $1 \times 10^4$ cells/cm$^2$ in MSC Attachment/Growth Medium. The cells were cultured in MSC Attachment/Growth Medium for 2-3 days, at which point the media was replaced with Adipogenesis Differentiation Medium (STEMPRO® Adipocyte Differentiation Basal Medium, STEMPRO® Adipogenesis supplement, 5 µg/mL gentamycin). The cells were further cultured for 21 days, with media replaced every 2-3 days. HCS LIPIDTOX™ Green Neutral Lipid staining was performed on day 17 according to the manufacturer's instructions, and the stained cells visualized under fluorescence microscope.

Figure 4A:
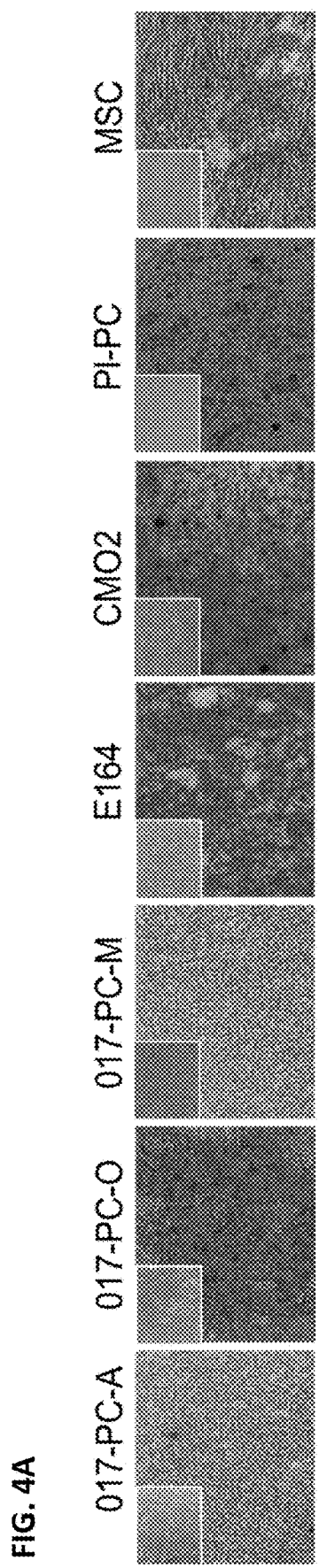
FIG. 4A consists of photo-micrograph images illustrating the osteogenic differentiation potential of 017-PC-0 cells and clonal pericyte lines E164 and CMO2.

Data are shown in FIG. 4 and summarized in FIG. 8. Neither 017-PC-A nor 017-PC-M cells displayed chondrogenic or osteogenic potential (FIG. 4a and data not shown). However, 017-PC-O cells, generated by further differentiation of 017-PC-A cells by culturing the 017-PC-A cells in MSC medium (DMEM/10% FBS) for 3 days, were capable of osteogenic differentiation (FIG. 4a). The differentiation potential was maintained through long-term passage, as both early (p1) and late (p21) passage 017-PC-O cells differentiated toward bone cells, though early passage cells were not as efficient. Both clonal lines E164 and CMO2 as well as the placental and brain vessel derived primary pericytes differentiated into osteocytes as demonstrated by Alizarin Red S staining (FIG. 4a and data not shown).

Figure 4B:
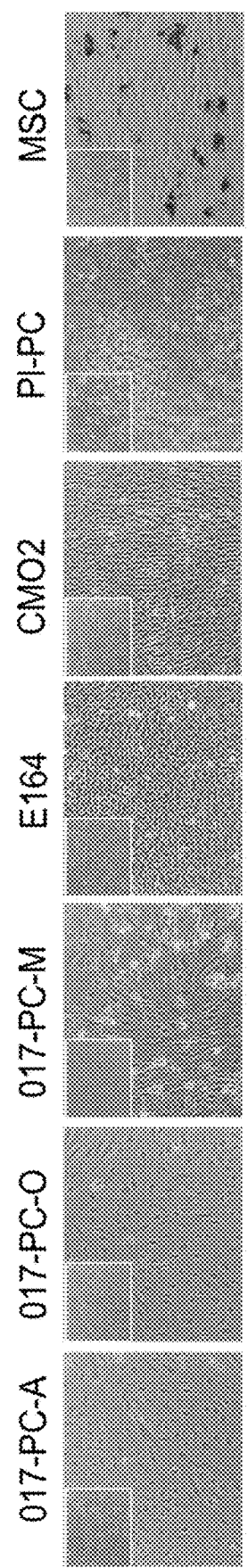
FIG. 4B consists of photo-micrograph images illustrating the lack of adipogenic potential by all hES-derived pericytes/perivascular stromal cells of the invention.

Adipogenic media used to differentiate bone marrow MSCs to fat cells did not result in differentiation of hES derived pericytes (017-PC-A, 017-PC-M, 017-PC-O and clonal lines E164 and CMO2) or primary pericytes (BV-PC and PL-PC) (FIG. 4b).

Example 5: In Vitro Angiogenic Potential—Tube Formation Assay

017-PC-A, 017-PC-M and 017-PC-O cells as well as clonal lines E164 and CMO2 were assessed for their angiogenic potential in vitro by testing the cells' ability to form tubular capillary-like structures on MATRIGEL®, either alone or in co-culture with endothelial cells. The tube formation assay on MATRIGEL® was similar to the assay used by Block et al. (2013 Stem Cells Dev. 2(17):2347-55.), with details below.

All cells were cultured in their corresponding growth media. At setup, the cells were harvested by treatment with ACCUTASE® for 5 minutes and quenched with their growth media. The harvested cells were transferred to a centrifuge tube and centrifuged at 100×g for 5-10 minutes. The formed pellets were resuspended in EGM-MV2 basal medium and counted. Endothelial cells (HUVEC) were labeled with green DiO dye and pericyte-like cells of the invention were pre-labeled with red DiL dye (both dyes from Life Technologies) by mixing 5 μL of dye with $1 \times 10^6$ cells in 1 mL media at 37° C. or 15 minutes. After labeling, the cells were washed twice in basal medium and resuspended in basal medium for a final concentration of $5 \times 10^5$ cells/mL.

The assay was set up on Growth Factor Reduced (GFR) MATRIGEL® in 96-well plates, with 50 μL of GFR MATRIGEL® coating per well. Endothelial cells and pericytes were added either alone or mixed at 3:1 ratio, respectively. The cells were seeded in triplicates with $7.5 \times 10^4$ viable cells per well. The cells were visualized under fluorescent microscope and images acquired beginning at 24 hours. Additional images were acquired at 48 and 72 hours, as indicated, and the experiment was continued up to 6 days to assess stability of the tube-like structures.

Figure 5A:
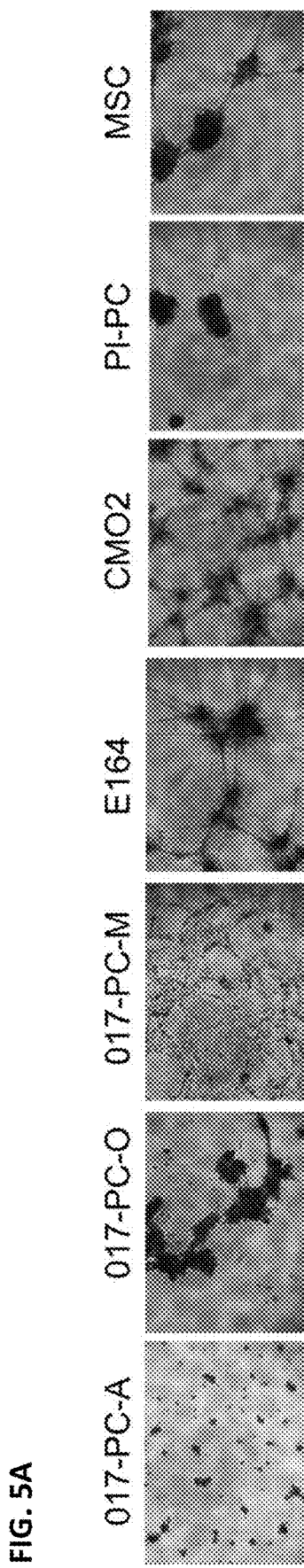
FIGS. 5A and 5B are photo-micrographs images illustrating the ability of 017-PC-M cells form tubular networks in vitro alone (FIG. 5a) or in co-culture with HUVEC cells (FIG. 5b).
Figure 5B:
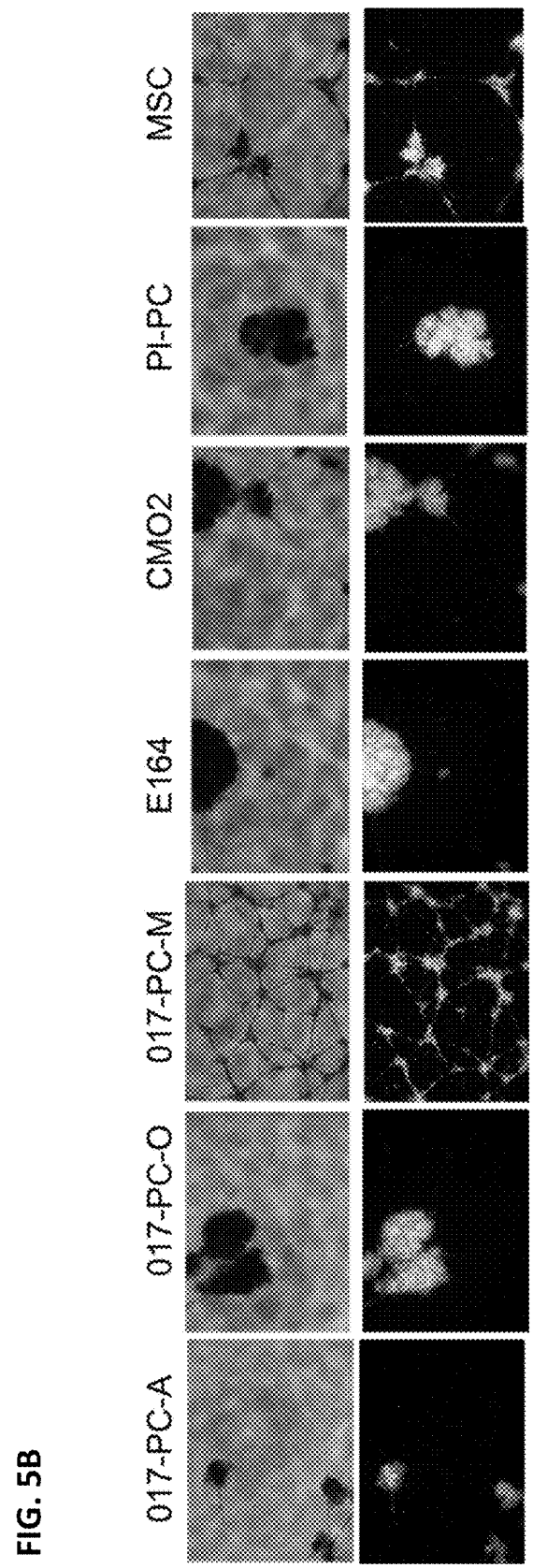
Figure 6:
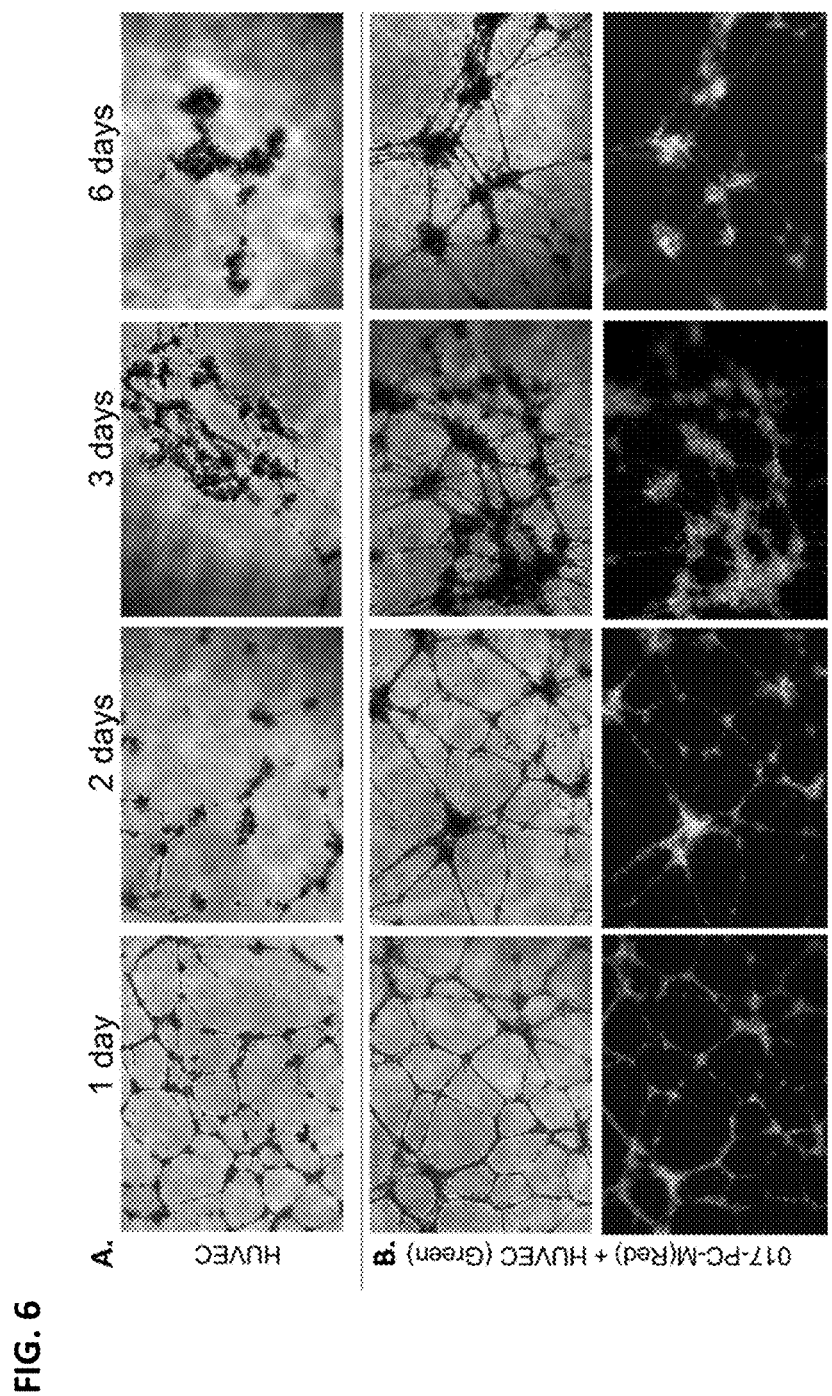
FIG. 6 is a photomicrograph illustrating the stabilizing effect of 017-PC-M cells on tubular networks formed by HUVEC cells.

The results are depicted in FIGS. 5 and 6. Of the pericyte-like cells tested, only 017-PC-M were able to form tube-like structures alone; 017-PC-O, CMO2, E164 and bone-marrow MSCs tended to form clusters connected through thin tubes whereas 017-PC-A and PL-PC cells did not form tubes at all (FIG. 5*a*). Similarly, the 017-PC-M cells formed tubular networks in co-culture with HUVEC cells, whereas the other pericyte-like/PSC cells tested formed little to no tubes when co-cultured with HUVEC (FIG. 5*b*). The tubular networks formed by HUVEC cells alone (in the absence of pericytes/perivascular stromal cells) did not persist and disintegrated after 24 hours (FIG. 6*a*). In contrast, the tubular networks formed by HUVEC cells+017-PC-M cells persisted at day 6 (FIG. 6*b*), indicating that the hESC-derived pericyte/perivascular stromal cells, 017-PC-M, support endothelial tube formation and stability.

Example 6: A Kit for Studying Angiogenesis In Vitro

A kit has been developed to provide a unique, robust co-culture assay to study angiogenesis in vitro. In this model system, we utilize a unique perivascular stromal cell line (017-PC-M) that when co-cultured with human umbilical vein endothelial cells (HUVEC) results in the rapid formation of large angiogenic networks with long-term stability of 4-6 days without the need for additional growth factors and complex media supplements.

Kit Materials and Additional Materials Needed:
Materials Included
$0.5 \times 10^6$ 017-PC-M cells
$1 \times 10^6$ HUVEC cells
VASCULIFE® basal media
VASCULIFE® supplemental factors: rh VEGF, rh bFGF, rh IGF-1, rh EGF, ascorbic acid, heparin sulfate, hydrocortisone hemisuccinate, L-glutamine and FBS
5 mM suramin hexasodium salt
Additional Materials Needed
T-150 tissue culture flasks
96-well plate
Growth-factor reduced MATRIGEL®
Media Preparation VASCULIFE® growth media: VASCULIFE® basal media containing supplemental factors with final concentrations as indicated below
rh VEGF—5 ng/mL
rh EGF—5 ng/mL
rh FGF—5 ng/mL
rh IGF-1-15 ng/mL
L-Glutamine—10 mM
Hydrocortisone hemisuccinate—1.0 μg/mL
Heparin sulfate—0.75 U/mL
Ascorbic acid—50 μg/mL
Fetal Bovine Serum—5% by volume
VASCULIFE® assay media: VASCULIFE® basal media plus 10 mM L-glutamine (final concentration)

Assay Protocol:
1. Four days (Day −4) prior to assay, HUVECs should be thawed and seeded at $3.5 \times 10^4$ cells per $cm^2$ into a 150 $cm^2$ tissue culture flask containing VASCULIFE® growth media. Incubate cells at 37° C. and 5% $CO_2$. Exchange full volume of media every 1-2 days.
2. Two days (Day −2) prior to assay, PC-M cells should be thawed and seeded at $10 \times 10^4$ cells per $cm^2$ into a 150 $cm^2$ tissue culture flask containing VASCULIFE® growth media. Incubate cells at 37° C. and 5% $CO_2$. Exchange full volume of media every 1-2 days.
3. At Day 0, prepare 96-well plate with MATRIGEL® coating of 50 μL per well. Let plate warm for at least 1 hour prior to seeding cells.
4. Prepare assay solution: dilute L-glutamine into VASCULIFE® medium.
5. On Day 0, harvest both HUVECs and PC-M cells. Recommended: Use 5-7.5 mL ACCUTASE® treatment for 3-5 minutes to detach cells, then quench Accutase® with an equivolume of Vasculife® growth media before pelleting cells.
6. Prepare VASCULIFE® assay media (500 μL per each triplicate condition).
7. Pellet cells at 250-350 rpm for 5 minutes at room temperature.
8. Decant media and re-suspend into 1 mL of VASCULIFE® assay media.
9. Measure cell concentration and viability:

|  | HUVECs | 017-PC-M cells |
|---|---|---|
| Cell concentration (cells per mL) |  |  |
| Viability (0.96 = 96%) |  |  |
| Live cell concentration (Total cell concentration × viability) |  |  |

10. Mix cells at a ratio of 3:1 HUVECs: 017-PC-M cells and seed at a final density of 37,500 cells per well. For one set of triplicates, mix approximately 85,000 HUVECs with 28,000 017-PC-M cells.
11. Allow co-culture to adhere at 37° C. for 3-4 hours.
12. After 3-4 hours at 37° C., the cells can then be treated with additional test reagents and imaged every 1-2 days starting at Day 1.

Expected Results

We typically observe average tube stability of 4-6 days in HUVEC+017-PC-M co-cultures in contrast with HUVEC cell monoculture, where the tubes start disintegrating after 24 hours. 017-PC-M cells alone show stable tube formation at 1-2 days in monoculture, but no stable tube formation at 4-6 days of monoculture. Addition of 50 µM Suramin (anti-angiogenic factor) will reduce tube formation by >90%.

Troubleshooting

Both 017-PC-M cells and HUVECs must be well dispersed prior to seeding. Expansion of these cells to >90% confluency may yield more cell clumps and inhibit tube formation in monocultures and/or co-cultures.

The ability of 017-PC-M cells to support tube stability requires that these cells be mixed with the endothelial target cell type at a ratio of no more than 3:1 endothelial cells to 017-PC-M cells. High cell seeding densities above 37,500 cells may result in formation of dense cell sheets and/or clusters with little to no tube formation.

Addition of basic FGF to the assay media at concentrations ≥10 ng/mL may result in increased cell proliferation and lead to formation of dense cell sheets and/or clusters with little to no tube formation in monocultures of HUVECs, monocultures of 017-PC-M cells and/or co-cultures.

Addition of VEGF to the assay media may inhibit formation of tubes in monocultures of HUVECs, monocultures of 017-PC-M cells and/or co-cultures for VEGF concentrations ≤2.5 ng/mL or ≥10 ng/mL.

REFERENCES

[1] Bergers G, Song S. The role of pericytes in blood-vessel formation and maintenance. Neuro Oncol 2005 7(4):452-64.
[2] Dore-Duffy P, Cleary K. Morphology and properties of pericytes. Methods Mol Biol 2011; 686:49-68.
[3] Sagare A P, Bell R D, Zhao Z, Ma Q, Winkler E A, Ramanathan A, Zlokovic B V. Pericyte loss influences Alzheimer-like neurodegeneration in mice. Nat Commun 2013; 4:2932.
[4] Winkler E A, Sengillo J D, Sullivan J S, Henkel J S, Appel S H, Zlokovic B V. Blood-spinal cord barrier breakdown and pericyte reductions in amyotrophic lateral sclerosis. Acta Neuropathol 2013 125(1):111-20.
[5] Yemisci M, Gursoy-Ozdemir Y, Vural A, Can A, Topalkara K, Dalkara T. Pericyte contraction induced by oxidative-nitrative stress impairs capillary reflow despite successful opening of an occluded cerebral artery. Nat Med 2009 15:1031-1037.
[6] Armulik A, Genové G, Betsholtz C. Pericytes: developmental, physiological, and pathological perspectives, problems, and promises. Dev Cell 2011 21(2):193-215.
[7] Corselli M, Crisan M, Murray I R, West C C, Scholes J, Codrea F, Khan N, Péault B. Identification of perivascular mesenchymal stromal/stem cells by flow cytometry. Cytometry A 2013 83(8):714-20.
[8] Dar A, Domev H, Ben-Yosef O, Tzukerman M, Zeevi-Levin N, Novak A, Germanguz I, Amit M, Itskovitz-Eldor J. Multipotent vasculogenic pericytes from human pluripotent stem cells promote recovery of murine ischemic limb. Circulation 2012 125(1):87-99.
[9] Orlova V V, Drabsch Y, Freund C, Petrus-Reurer S, van den Hil F E, Muenthaisong S, Dijke P T, Mummery C L. Functionality of endothelial cells and pericytes from human pluripotent stem cells demonstrated in cultured vascular plexus and zebrafish xenografts. Arterioscler Thromb Vasc Biol 2014 34(1):177-186.
[10] Birbrair A, Zhang T, Wang Z M, Messi M L, Enikolopov G N, Mintz A, Delbono O. Role of pericytes in skeletal muscle regeneration and fat accumulation. Stem Cells Dev 2013 22(16):2298-314.
[11] Birbrair A, Zhang T, Wang Z M, Messi M L, Olson J D, Mintz A, Delbono O. Type-2 Pericytes Participate in Normal and Tumoral Angiogenesis. Am J Physiol Cell Physiol 2014 Apr. 30. [Epub ahead of print].
[12] Odaka C. Localization of mesenchymal cells in adult mouse thymus: their abnormal distribution in mice with disorganization of thymic medullary epithelium. J Histochem Cytochem. 2009 57(4):373-382.
[13] Fu J, Gerhardt H, McDaniel J M, Xia B, Liu X, Ivanciu L, Ny A, Hermans K, Silasi-Mansat R, McGee S, Nye E, Ju T, Ramirez M I, Carmeliet P, Cummings R D, Lupu F, Xia L. Endothelial cell O-glycan deficiency causes blood/lymphatic misconnections and consequent fatty liver disease in mice. J Clin Invest. 2008 118(11): 3725-37.
[14] West M D, Sargent R G, Long J, Brown C, Chu J S, Kessler S, Derugin N, Sampathkumar J, Burrows C, Vaziri H, Williams R, Chapman K B, Larocca D, Loring J F, Murai J. The ACTCellerate initiative: large-scale combinatorial cloning of novel human embryonic stem cell derivatives. Regen Med 2008 3(3):287-308.
[15] Chen S T, Hsu C Y, Hogan E L, Maricq H, Balentine J D. A model of focal ischemic stroke in the rat: reproducible extensive cortical infarction. Stroke 1986 17(4): 738-43.
[16] Limbourg A, Korff T, Napp L C, Schaper W, Drexler H, Limbourg F P. Evaluation of postnatal arteriogenesis and angiogenesis in a mouse model of hind-limb ischemia. Nat Protoc 2009 4(12):1737-46.
[17] Lai A K, Lo A C. Animal models of diabetic retinopathy: summary and comparison. J Diabetes Res 2013 2013:106594.
[18] Zaragoza C, Gomez-Guerrero C, Martin-Ventura J L, Blanco-Colio L, Lavin B, Mallavia B, Tarin C, Mas S, Ortiz A, Egido J. Animal models of cardiovascular diseases. J Biomed Biotechnol 2011 2011:497841.
[19] Garbuzova-Davis S, Sanberg P R. Blood-CNS Barrier Impairment in ALS patients versus an animal model. Front Cell Neurosc 2014 8:21.
[20] Daneman R, Zhou L, Kebede A A, Barres B A. Pericytes are required for blood-brain barrier integrity during embryogenesis. Nature 2010 468(7323):562-6.
[21] Armulik A, Genové G, Mäe M, Nisancioglu M H, Wallgard E, Niaudet C, He L, Norlin J, Lindblom P, Strittmatter K, Johansson B R, Betsholtz C. Pericytes regulate the blood-brain barrier. Nature 2010 468(7323): 557-61.
[22] ElAli A, Thériault P, Rivest S. The role of pericytes in neurovascular unit remodeling in brain disorders. Int J Mol Sci. 2014 15(4):6453-74.
[23] Wilcock DM1, Vitek M P, Colton C A. Vascular amyloid alters astrocytic water and potassium channels in mouse models and humans with Alzheimer's disease. Neuroscience 2009 159(3):1055-69.

What is claimed is:

1. An isolated population of pericyte progenitor cells comprising a CD146+/CD73+/CD133+/CD31− expression profile, wherein the cells express podoplanin and are CD34− or CD34+, and wherein the cells are not adipogenic when cultured in adipogenesis differentiation medium, are osteogenic when cultured in mesenchymal stem cell medium, and are angiogenic when cultured in endothelial cell growth medium.

2. The isolated population of pericyte progenitor cells of claim 1, wherein the cells further express one or more of markers chosen from CD90, CD105, PDGFRβ and NG2.

3. The isolated population of pericyte progenitor cells of claim 1, wherein the cells are CD34−.

4. A kit comprising the isolated population of pericyte progenitor cells of claim 1 and endothelial cells.

5. The kit of claim 4, wherein the pericyte progenitor cells and the endothelial cells are at a ratio of 1:3.

6. The kit of claim 5, wherein the endothelial cells are HUVEC cells.

7. The kit of claim 4, further comprising culture media, optionally also comprising substrate or extracellular matrix for culturing cells.

8. The kit of claim 7, further comprising an anti- or pro-angiogenic factor.

* * * * *